US011649317B2

(12) United States Patent
Masubuchi et al.

(10) Patent No.: US 11,649,317 B2
(45) Date of Patent: May 16, 2023

(54) POLYURETHANE GEL COMPOSITION AND USE THEREOF

(71) Applicant: KOSE Corporation, Tokyo (JP)

(72) Inventors: Yuji Masubuchi, Tokyo (JP); Ryo Hagino, Tokyo (JP); Hisanori Ishita, Ishikawa (JP)

(73) Assignee: KOSE Corporation, Tokyo (JP)

(*) Notice: Subject to any disclaimer, the term of this patent is extended or adjusted under 35 U.S.C. 154(b) by 111 days.

(21) Appl. No.: 16/497,956

(22) PCT Filed: Mar. 30, 2018

(86) PCT No.: PCT/JP2018/013607
§ 371 (c)(1),
(2) Date: Sep. 26, 2019

(87) PCT Pub. No.: WO2018/181899
PCT Pub. Date: Oct. 4, 2018

(65) Prior Publication Data
US 2021/0102025 A1  Apr. 8, 2021

(30) Foreign Application Priority Data
Mar. 31, 2017 (WO) .................. PCT/JP2017/013748

(51) Int. Cl.
*C08G 18/65* (2006.01)
*C08G 18/62* (2006.01)
(Continued)

(52) U.S. Cl.
CPC .......... *C08G 18/6511* (2013.01); *A61K 8/022* (2013.01); *A61K 8/0229* (2013.01);
(Continued)

(58) Field of Classification Search
CPC ............... A61Q 1/10; A61Q 1/04; A61Q 5/06
See application file for complete search history.

(56) References Cited

U.S. PATENT DOCUMENTS 5,925,724 A     7/1999  Cenens et al.
2002/0122781 A1* 9/2002  Pinzon .................. A61K 8/416
                                                                424/70.11
(Continued)

FOREIGN PATENT DOCUMENTS

EP    1013264 A1    6/2000
JP    H8-218097     8/1996
(Continued)

OTHER PUBLICATIONS

Shibayama, Mitsuhiro. "New Development of Gel Physics and Chemistry." Journal of Japan Physics Association, vol. 72, No. 4, 2017, pp. 226-227.

*Primary Examiner* — Jianfeng Song
(74) *Attorney, Agent, or Firm* — Occhiuti & Rohlicek LLP

(57) ABSTRACT

Provided is a polyurethane gel composition containing A and B below. Here, A represents a polyurethane obtained by reaction of (a) a hydrogenated polybutadiene having isocyanate groups at the terminals and (b) a glycol represented by HO—$R_3$—OH (wherein $R_3$ represents a linear or branched C2 to C6 alkylene group optionally having an ether bond), or A represents a polyurethane obtained by reaction of (c) a hydrogenated polybutadiene having hydroxyl groups at the terminals, (d) a diisocyanate compound, and the (b) glycol represented by HO—$R_3$—OH (wherein $R_3$ represents a linear or branched C2 to C6 alkylene group optionally having an ether bond), and B represents an oil agent. The polyurethane gel composition of the present invention is particularly useful as a raw material for cosmetics since a film of an oil-soluble gel obtained using the polyurethane gel composition is exceptionally excellent in any point of transparency, high gloss, elasticity, and resilience.

15 Claims, 2 Drawing Sheets

SCHEMATIC DIAGRAM OF MEASUREMENT

(51) Int. Cl.
| | |
|---|---|
| C08G 18/32 | (2006.01) |
| C08G 18/72 | (2006.01) |
| C08J 3/11 | (2006.01) |
| C08L 91/06 | (2006.01) |
| A61K 8/87 | (2006.01) |
| A61K 8/891 | (2006.01) |
| A61K 8/92 | (2006.01) |
| A61K 8/73 | (2006.01) |
| A61Q 19/00 | (2006.01) |
| A61Q 19/10 | (2006.01) |
| A61Q 5/06 | (2006.01) |
| A61Q 1/10 | (2006.01) |
| A61Q 17/04 | (2006.01) |
| A61Q 1/12 | (2006.01) |
| A61K 8/02 | (2006.01) |
| A61K 8/06 | (2006.01) |
| A61K 8/19 | (2006.01) |
| A61K 8/25 | (2006.01) |
| A61K 8/26 | (2006.01) |
| A61K 8/27 | (2006.01) |
| A61K 8/29 | (2006.01) |
| A61K 8/31 | (2006.01) |
| A61K 8/34 | (2006.01) |
| A61K 8/36 | (2006.01) |
| A61K 8/365 | (2006.01) |
| A61K 8/37 | (2006.01) |
| A61K 8/41 | (2006.01) |
| A61K 8/44 | (2006.01) |
| A61K 8/49 | (2006.01) |
| A61K 8/55 | (2006.01) |
| A61K 8/81 | (2006.01) |
| A61K 8/88 | (2006.01) |
| A61Q 1/04 | (2006.01) |
| A61Q 1/06 | (2006.01) |
| A61Q 1/14 | (2006.01) |
| C08G 18/73 | (2006.01) |

(52) U.S. Cl.
CPC .............. *A61K 8/062* (2013.01); *A61K 8/064* (2013.01); *A61K 8/19* (2013.01); *A61K 8/25* (2013.01); *A61K 8/26* (2013.01); *A61K 8/27* (2013.01); *A61K 8/29* (2013.01); *A61K 8/31* (2013.01); *A61K 8/342* (2013.01); *A61K 8/345* (2013.01); *A61K 8/36* (2013.01); *A61K 8/361* (2013.01); *A61K 8/365* (2013.01); *A61K 8/37* (2013.01); *A61K 8/375* (2013.01); *A61K 8/41* (2013.01); *A61K 8/416* (2013.01); *A61K 8/44* (2013.01); *A61K 8/498* (2013.01); *A61K 8/4973* (2013.01); *A61K 8/553* (2013.01); *A61K 8/73* (2013.01); *A61K 8/731* (2013.01); *A61K 8/732* (2013.01); *A61K 8/8111* (2013.01); *A61K 8/8147* (2013.01); *A61K 8/8176* (2013.01); *A61K 8/87* (2013.01); *A61K 8/88* (2013.01); *A61K 8/891* (2013.01); *A61K 8/92* (2013.01); *A61K 8/922* (2013.01); *A61K 8/925* (2013.01); *A61K 8/927* (2013.01); *A61Q 1/04* (2013.01); *A61Q 1/06* (2013.01); *A61Q 1/10* (2013.01); *A61Q 1/12* (2013.01); *A61Q 1/14* (2013.01); *A61Q 5/06* (2013.01); *A61Q 17/04* (2013.01); *A61Q 19/007* (2013.01); *A61Q 19/10* (2013.01); *C08G 18/3206* (2013.01); *C08G 18/6208* (2013.01); *C08G 18/73* (2013.01); *C08J 3/11* (2013.01); *C08L 91/06* (2013.01); A61K 2800/48 (2013.01); A61K 2800/594 (2013.01); A61K 2800/623 (2013.01); A61K 2800/651 (2013.01); A61K 2800/87 (2013.01); C08L 2207/324 (2013.01)

(56) References Cited

U.S. PATENT DOCUMENTS

| | | | |
|---|---|---|---|
| 2002/0157193 | A1 | 10/2002 | Legrand et al. |
| 2003/0192134 | A1 | 10/2003 | Desenne et al. |
| 2004/0141942 | A1* | 7/2004 | Rollat ............. A61Q 5/06 424/70.17 |
| 2007/0148120 | A1* | 6/2007 | Omura ............. C08L 75/04 424/70.16 |
| 2016/0177017 | A1* | 6/2016 | Miyata ............. A61K 8/91 424/401 |

FOREIGN PATENT DOCUMENTS

| | | |
|---|---|---|
| JP | H9-228294 | 9/1997 |
| JP | H11-071391 | 3/1999 |
| JP | 11-507975 | 7/1999 |
| JP | 2000-63235 | 2/2000 |
| JP | 2000-178137 | 6/2000 |
| JP | 2000-230120 | 9/2000 |
| JP | 2000-239120 A | 9/2000 |
| JP | 2001-287309 | 10/2001 |
| JP | 2002-241250 | 8/2002 |
| JP | 2003-226626 | 8/2003 |
| JP | 2004-505137 | 2/2004 |
| JP | 2004-515466 | 5/2004 |
| JP | 2005-15457 | 1/2005 |
| JP | 2008-88099 | 4/2008 |
| JP | 2009-235036 | 10/2009 |
| JP | 4802136 | 8/2011 |
| WO | 02/09655 | 2/2002 |
| WO | 02/10243 | 2/2002 |
| WO | 2006/126470 | 11/2006 |
| WO | 2016090081 A1 | 6/2016 |

\* cited by examiner

[Fig. 1]
SCHEMATIC DIAGRAM OF MEASUREMENT
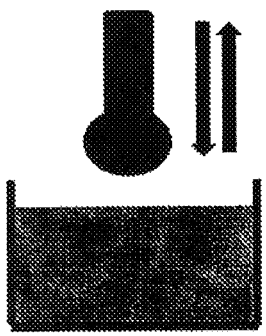

[Fig. 2]
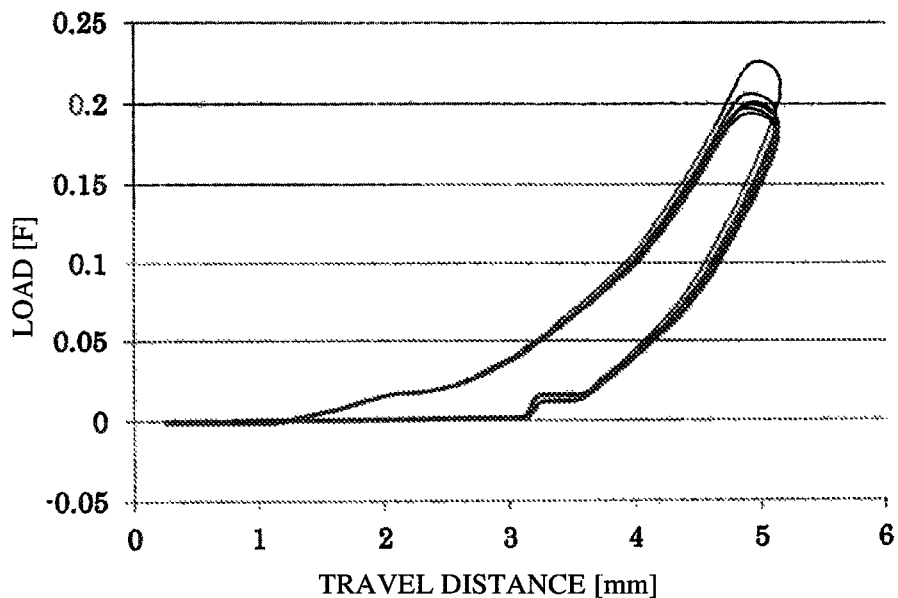
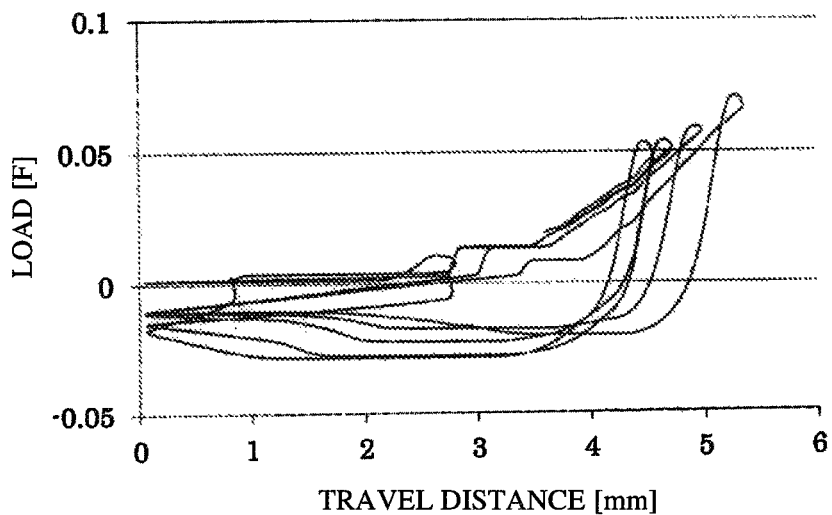

POLYURETHANE GEL COMPOSITION AND USE THEREOF

CROSS REFERENCE TO RELATED APPLICATIONS

This application is the national phase under 35 USC 371 of international Application No. PCT/JP2018/013607, filed Mar. 30, 2018, which is a continuation of international Application No. PCT/JP2017/013748 filed Mar. 31, 2017.

TECHNICAL FIELD

The present invention relates to a novel polyurethane gel composition having high elasticity while having both strength and flexibility, and to use thereof, particularly, use for cosmetics.

BACKGROUND ART

Conventionally, polyurethanes have been used as thermoplastic resins, adhesives, water-soluble gelling agents, or the like (see Patent Documents below). As such a thermoplastic resin, use of a resin sheet produced using polyurethane acrylate having a hydrogenated polybutadiene backbone or polyurethane acrylate having a polybutadiene backbone as a glazed printing sheet has been proposed, for example (Patent Document 1). Further, there has been proposed a composition for producing a thermoplastic polyurethane that contains polydiene diol having 1.6 to 2 terminal hydroxyl groups per molecule and a number-average molecular weight of 500 to 20,000, isocyanate having 2 isocyanate groups per molecule, and a low-molecular weight chain extender having 2 hydroxyl groups per molecule, as required, and has good physical properties and excellent weather resistance (Patent Document 2).

As such an adhesive, a decorative board provided with an adhesive layer or an adhesive layer and a base coat layer, and a transfer layer on a base material, wherein the adhesive layer is obtained from an adhesive consisting of a hydroxyl group-containing polybutadiene polymer and an organic polyisocyanate has been proposed, for example, and it has been taught that the adhesive can contain a hydroxyl group-containing resin other than the hydroxyl group-containing polybutadiene polymer (such as a resin using ethylene glycol as a starting material), as required (Patent Document 3).

As such a water-soluble gelling agent, an automatic fragrance/cleaner material for flush toilets consisting of a water-soluble solid polyurethane resin (D) derived from a water-soluble polyoxyalkylene polyol (A), a water-insoluble polyol (B) having a number-average molecular weight of 500 to 2,000, and an organic polyisocyanate (C) at a weight ratio (A):(B) of (99.9 to 85.0):(0.1 to 15.0) has been proposed, for example (Patent Document 4).

Polyurethanes have been also used for various applications in the field of cosmetics. For example, a cosmetic composition containing an associative thickener consisting of a hydrophilic compound having a urethane bond (copolymer having a hydrophilic moiety as the backbone and a hydrophobic moiety at the terminals) has been proposed (Patent Document 5). Further, a mascara product provided with: a storage including a composition that contains an aqueous medium and a film forming polyurethane in the form of solid particles dispersed in the aqueous medium, has a viscosity in the range of 5 Pa·s to 18 Pa·s at a temperature of 25° C. and a shear rate of 200 s$^{-1}$, and is free from waxes; and a sealing device having an applicator has been proposed (Patent Document 6). Further, there have been proposed: a viscous emulsion composition containing a physiologically acceptable medium thickened by an associative polyurethane, the medium including an aqueous phase and a liquid fat phase in the emulsion, the composition having a consistency for care, treatment, or makeup of human faces and body skins, keratin fibers such as eyelashes, eyebrows, and hair, or further lips (Patent Document 7); a cosmetic patch including a gel layer consisting of a tacky polyurethane gel having a hydrophilic alkylene oxide segment and a hydrophobic alkylene oxide segment, most to all of the segments being in liquid form at normal temperature, the gel layer containing vitamins (Patent Document 8); an elastic gelatinous oily cosmetic containing a partially crosslinked organopolysiloxane polymer, solid oil, and powder (for example, polyurethane powder) (Patent Document 9); a cosmetic containing polyurethane gel particles enclosing a functional component and/or a design component, wherein the gel particles are polyurethane gel particles (particles C) formed by coating the surfaces of three-dimensionally crosslinked polyurethane gel particles (particles A) obtained by copolymerizing polyisocyanate, a compound having an active hydrogen group in the molecule, and a reaction product of polysiloxane having an active hydrogen group in the molecule and/or the polysiloxane and lactone, at least any one of which is trifunctional or more, with colloidal polyurea particles (particles B) deposited from a colloidal polyurea-non-aqueous solvent solution (Patent Document 10); and the like.

PRIOR ART DOCUMENTS

Patent Documents

[Patent Document 1] Japanese Unexamined Patent Application Publication No. 9-228294
[Patent Document 2] Japanese Unexamined Patent Application Publication (Translation of PCT Application) No. 11-507975
[Patent Document 3] Japanese Unexamined Patent Application Publication No. 2001-287309
[Patent Document 4] Japanese Unexamined Patent Application Publication No. 8-218097
[Patent Document 5] Japanese unexamined Patent Application Publication No. 2000-239120
[Patent Document 6] Japanese Unexamined Patent Application Publication No. 2000-178137
[Patent Document 7] Japanese Unexamined Patent Application Publication No. 2000-63235
[Patent Document 8] Japanese Unexamined Patent Application Publication No. 2005-15457
[Patent Document 9] Japanese Unexamined Patent Application Publication No. 2008-88099
[Patent Document 10] Japanese Patent No. 4802136

SUMMARY OF THE INVENTION

Object to be Solved by the Invention

The inventors have repeatedly investigated conventional techniques in order to solve the problems of skins or eyelids such as wrinkles, sags, dark spots, and dullness. Examples of countermeasures to such wrinkles, sags, dark spots, dullness, and the like in the conventional techniques include countermeasures using various dosage forms such as powder solid and oily solid forms. However, a powder solid containing a pearl agent has disadvantages of unnatural glare, thereby emphasizing unevenness and making wrinkles and the like noticeable conversely, and poor adhesion of pearl. Meanwhile, an oily solid dosage form has disadvantages of containing a large amount of crystalline components, thereby resulting in insufficient gloss and occurrence of twists on unevenness (gap of double eyelid) with the elapse of time. Accordingly, when producing a cosmetic for improving wrinkles, sags, dark spots, and dullness, it is necessary to correspond to faces and eyelids that three-dimensionally and intensely move. From such viewpoints, the inventors aimed to develop a cosmetic film having the following characteristics of:

(1) having flexibility to motions and self-repairing ability, wherein, even if unevenness occurs, it naturally recovers, and the surface of the cosmetic film is always smooth, that is, the film is not twisted;
(2) having gloss and thickness, that is, brightness by wet gloss; and
(3) having an excellent lasting effect of a cosmetic film.

The inventors repeatedly researched resilient materials using silicone rubbers, polysaccharides, and aqueous polyurethanes. However, it was found that these materials have disadvantages to be solved together with advantages. That is, silicone rubber is a soft gel but has disadvantages of lack of gloss and lack of resilience. A polysaccharide gel has high transparency and high gel strength but has disadvantages of low elasticity and low resilience. An aqueous polyurethane gel is transparent and has high elasticity and high resilience but has serious disadvantages of limited color gamut due to the need for water, lack of gloss, and lack of the lasting effect of the cosmetic film.

Generally, polyurethanes are known to be obtained by reaction of a diisocyanate and a polyol, and polyurethanes consisting of a hydrogenated polybutene and a polyhydric alcohol fall within a category of well-known techniques. However, there are no examples of using polyurethanes as oil-soluble gelling agents.

Means to Solve the Object

Accordingly, the inventors have intensively repeated research and development in order to obtain a transparent cosmetic film having high gloss, elasticity, and resilience, and an excellent makeup lasting effect.

As a result, the inventors have found that a polyurethane gel composition having elasticity and resilience is obtained by mixing an oil agent with a polyurethane obtained by reaction of (a) a hydrogenated polybutadiene having isocyanate groups at the terminals, and (b) a glycol represented by HO—$R_3$—OH (wherein $R_3$ represents a linear or branched C2 to C6 alkylene group optionally having an ether bond), or a polyurethane obtained by reaction of (c) a hydrogenated polybutadiene having hydroxyl groups at the terminals, (d) a diisocyanate compound, and the (b) glycol represented by HO—$R_3$—OH (wherein $R_3$ represents a linear or branched C2 to C6 alkylene group optionally having an ether bond). They have found that use of the polyurethane gel composition for cosmetics allows a cosmetic film having excellent gloss to be obtained and enhances the effect of suppressing makeup deterioration or the like with time due to the motions of skins, eyelids, and the like (makeup lasting effect). The present invention has been accomplished based on such findings.

That is, the present invention is as follows.

(1) A polyurethane gel composition comprising A and B, wherein A represents a polyurethane obtained by reaction of (a) a hydrogenated polybutadiene having isocyanate groups at the terminals and (b) a glycol represented by HO—$R_3$—OH (wherein $R_3$ represents a linear or branched C2 to C6 alkylene group optionally having an ether bond), or A represents a polyurethane obtained by reaction of (c) a hydrogenated polybutadiene having hydroxyl groups at the terminals, (d) a diisocyanate compound, and the (b) glycol represented by HO—$R_3$—OH (wherein $R_3$ represents a linear or branched C2 to C6 alkylene group optionally having an ether bond), and B represents an oil agent.

(2) The composition according to (1), wherein (a) in A is an isocyanate compound obtained by reaction of the (c) hydrogenated polybutadiene having hydroxyl groups at the terminals and the (d) diisocyanate compound.

(3) The composition according to (1) or (2), wherein (d) in A is a diisocyanate compound represented by OCN—$R_2$—NCO (wherein $R_2$ represents a C2 to C6 alkylene).

(4) The composition according to any one of (1) to (3), wherein (a) in A is an isocyanate compound represented by formula (1):

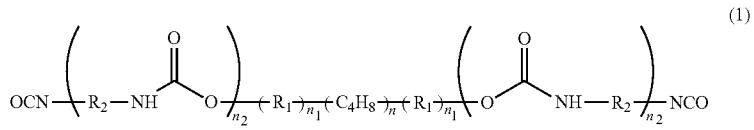

(wherein $R_1$ and $R_2$ each independently represent a $C_1$ to $C_6$ alkylene group, n represents an integer of 10 to 100, and $n_1$ and $n_2$ each independently represent 0 or 1).

(5) The composition according to any one of (1) to (4), wherein (a) in A is an isocyanate compound represented by formula (2):

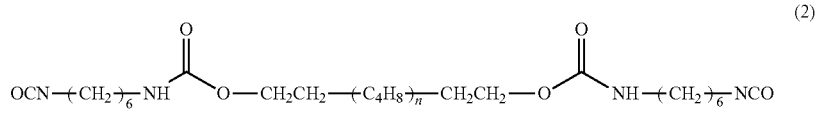

(wherein n represents an integer of 10 to 100).

(6) The composition according to (2), wherein
the (c) hydrogenated polybutadiene having hydroxyl groups at the terminals is

  (3)

(wherein n represents an integer of 10 to 100),
the (d) diisocyanate compound is

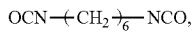  (4)

and
the (c) glycol represented by HO—$R_3$—OH is

HO—$CH_2$—$CH_2$—OH  (5).

(7) The composition according to (1), wherein the polyurethane represented by A is an oil-soluble polyurethane.
(8) The composition according to (1), wherein the polyurethane represented by A has an average molecular weight (Mw) of 10000 to 100000.

(9) The composition according to (1), wherein the oil agent represented by B is an oil agent in liquid form at 25° C.
(10) The composition according to (1), wherein the oil agent represented by B is one or more selected from a hydrocarbon oil, an ester oil having 0 or 1 hydroxyl group, and a silicone oil.

(11) The composition according to (1), wherein the polyurethane represented by A is contained in an amount of 1 to 35 mass %.
(12) The composition according to (1), wherein the oil agent represented by B is contained in an amount of 65 to 99 mass %.
(13) The composition according to any one of (1) to (12), wherein a gel obtained by dissolving 30 parts of the polyurethane gel composition according to any one of (1) to (12) and 70 parts of liquid paraffin by heating at 85° C., followed by cooling, has a load of 0.20 to 10.00 N (Newton) when a needle with a 2-cm-diameter spherical adapter is allowed to penetrate 10 mm at 2 cm/min.
(14) The composition according to any one of (1) to (13), having gel resilience.
(15) The composition according to any one of (1) to (14), having transmittance at a wavelength of 700 nm of 90% or more.
(16) A cosmetic comprising the composition according to any one of (1) to (15).

(17) A method for producing a polyurethane gel composition containing A and B (wherein A represents a polyurethane, and B represents an oil agent), the method comprising performing polyaddition reaction by adding (a) a hydrogenated polybutadiene having isocyanate groups at the terminals and (b) a glycol represented by HO—$R_3$—OH (wherein $R_3$ represents a linear or branched C2 to C6 alkylene group optionally having an ether bond), which serve as A, to the oil agent represented by B.
(18) The method according to (17), wherein (a) in A is an isocyanate compound obtained by reaction of (c) a hydrogenated polybutadiene having hydroxyl groups at the terminals and (d) a diisocyanate compound.
(19) The method according to (17), wherein the polyurethane represented by A is a polyurethane obtained by reaction of the (c) hydrogenated polybutadiene having hydroxyl groups at the terminals, the (d) diisocyanate compound, and the (b) glycol represented by HO—$R_3$—OH (wherein $R_3$ represents a linear or branched C2 to C6 alkylene group optionally having an ether bond).
(20) The method according to (18) or (19), wherein (d) in A is a diisocyanate compound represented by OCN—$R_2$—NCO (wherein $R_2$ represents a C2 to C6 alkylene).
(21) The method according to (17), (18), or (20), wherein (a) in A is an isocyanate compound represented by formula (1):

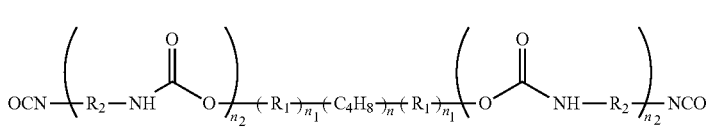  (1)

(wherein $R_1$ and $R_2$ each independently represent a $C_1$ to $C_6$ alkylene group, n represents an integer of 10 to 100, $n_1$ and $n_2$ each independently represent 0 or 1).
(22) The method according to (17), (18), (20), or (21), wherein (a) in A is an isocyanate compound represented by formula (2):

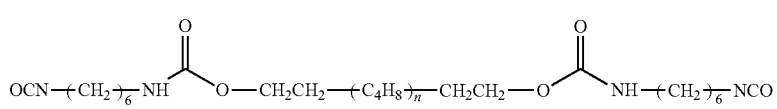  (2)

(wherein n represents an integer of 10 to 100).
(23) The method according to (20) or (21), wherein the (c) hydrogenated polybutadiene having hydroxyl groups at the terminals is

  (3)

(wherein n represents an integer of 10 to 100), the (d) diisocyanate compound is

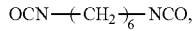  (4)

and the (b) glycol represented by HO—$R_3$—OH is

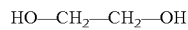  (5).

(24) The method according to (17) or (19), wherein the polyurethane represented by A is an oil-soluble polyurethane.
(25) The method according to (17) or (19), wherein the polyurethane represented by A has an average molecular weight (Mw) of 10000 to 100000.
(26) The method according to (17), wherein the oil agent represented by B is an oil agent in liquid form at 25° C.
(27) The method according to (26), wherein the oil agent represented by B is one or more selected from hydrocarbon oil, ester oil having 0 or 1 hydroxyl group, and silicone oil.
(28) The method according to (17) or (19), wherein the polyurethane represented by A is contained in an amount of 1 to 35 mass %.
(29) The method according to (17), wherein the oil agent represented by B is contained in an amount of 65 to 99 mass %.
(30) The method according to any one of (17) to (29), wherein a gel obtained by dissolving 30 parts of the polyurethane gel composition according to any one of (1) to (12) and 70 parts of liquid paraffin by heating at 85° C., followed by cooling, has a load of 0.20 to 10.00 N when a needle with a 2-cm-diameter spherical adapter is allowed to penetrate 10 mm at 2 cm/min.
(31) The method according to any one of (17) to (30), wherein the polyurethane gel composition has a gel resilience.
(32) The method according to any one of (17) to (31), wherein the polyurethane gel composition has a transmittance at a wavelength of 700 nm of 90% or more.

Effect of the Invention

The polyurethane gel composition of the present invention is exceptionally excellent in any point of transparency, high gloss, elasticity, and resilience, and thus the polyurethane gel composition of the present invention is useful as a base material for cosmetics to be applied to portions of the skin that frequently move, such as a body oil, a makeup base, a sunscreen, and an eye color.

BRIEF DESCRIPTION OF DRAWINGS

FIG. 1 is a schematic diagram showing a method for measuring the self-resilience of the polyurethane gel of the present invention obtained in Production Example 2 and the dextrin fatty acid ester gel obtained in Production Comparative Example 2.

FIG. 2 includes graphs showing the results of measuring the self-resilience of each of the polyurethane gel of the present invention obtained in Production Example 2 and the dextrin fatty acid ester gel obtained in Production Comparative Example 2.

MODE OF CARRYING OUT THE INVENTION

A polyurethane gel composition of the present invention containing A and B includes the following compositions.

Composition 1

A composition containing: a polyurethane obtained by reaction of (a) a hydrogenated polybutadiene having isocyanate groups at the terminals and (b) a glycol represented by HO—$R_3$—OH (wherein $R_3$ represents a linear or branched C2 to C6 alkylene group optionally having an ether bond) as A, and an oil agent as B.

Composition 2

A composition containing: a polyurethane obtained by reaction of (c) a hydrogenated polybutadiene having hydroxyl groups at the terminals, (d) a diisocyanate compound, and the (b) glycol represented by HO—$R_3$—OH (wherein $R_3$ represents a linear or branched C2 to C6 alkylene group optionally having an ether bond) as A, and an oil agent as B.

In the present invention, the "terminals" mean "both terminals".

The (a) in the A used in Composition 1 is not specifically limited, as long as it is a hydrogenated polybutadiene having isocyanate groups at the terminals. For example, a compound represented by formula (1) below is shown:

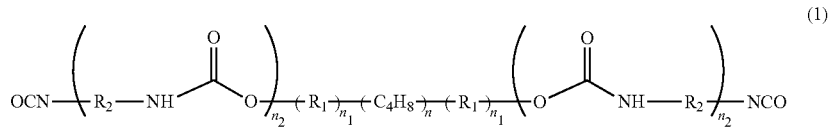

(1)

(wherein $R_1$ and $R_2$ each independently represent a $C_1$ to $C_6$ alkylene group, n represents an integer of 10 to 100, and $n_1$ and $n_2$ each independently represent 0 or 1).

$R_1$ and $R_2$ each independently represent a $C_1$ to $C_6$ alkylene group, that is, they may be the same or different, and the alkylene may have a linear or branched chain. Examples of the $C_1$ to $C_6$ alkylene group include methylene, ethylene, n-propylene, n-butylene, and n-hexylene.

Further, n represents an integer of 10 to 100, and a more preferable range of n is 15 to 55.

Further, $n_1$ and $n_2$ each independently represent 0 or 1, that is, they may be the same or different.

There are various types of the structure of the repeating unit "$C_4H_8$" in the hydrogenated polybutadiene portion in formula (1) above (formula (6) below)

(6)

for example, as shown below:

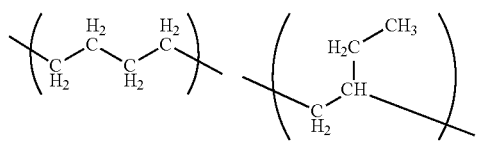

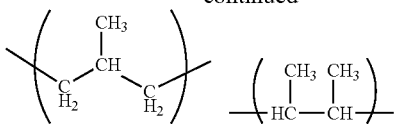

The hydrogenated polybutadiene portion in the hydrogenated polybutadiene having isocyanate groups at the terminals used in the present invention may consist of only one of the repeating units shown above as examples or may contain two or more types of the repeating units regularly or randomly. Even if the three-dimensional structures of the repeating units "C₄H₈" constituting the hydrogenated polybutadiene portion are the same or different, all the structures in which the hydrogenated polybutadiene portion represented by formula (6) are included in the present invention.

Examples of the hydrogenated polybutadiene represented by formula (1) and having isocyanate groups at the terminals include a compound represented by formula (2) below:

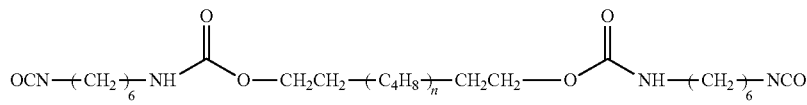

(wherein n represents an integer of 10 to 100).

The compound of formula (2) corresponds to the case where $R_1$ is an ethylene group, $R_2$ is a hexamethylene group, and $n_1=n_2=1$ is satisfied, in the hydrogenated polybutadiene having isocyanate groups at the terminals of formula (1).

Examples of the (b) glycol represented by HO—$R_3$—OH (wherein $R_3$ represents a linear or branched C2 to C6 alkylene group optionally having an ether bond) in the A to be used in Compositions 1 and 2 include ethylene glycol (HOCH₂CH₂OH), propylene glycol (HOCH₂CH(OH)CH₃), 1,3-butylene glycol (HOCH₂CH₂CH(OH)CH₃), and diethylene glycol (HOCH₂CH₂OCH₂CH₂OH).

The (c) hydrogenated polybutadiene having hydroxyl groups at the terminals in the A used in Composition 2 is not specifically limited. For example, a compound represented by formula (3) below is shown:

(wherein n represents an integer of 10 to 100).

In formula (3), the hydrogenated polybutadiene portion (formula (6)) has the same meaning as above.

Further, examples of the (d) diisocyanate compound used in Composition 2 can include hexamethylene diisocyanate, 1,3-bis(isocyanatomethyl)benzene, 1,3-bis(isocyanatomethyl)cyclohexane, 2,4-toluene diisocyanate, and 2,6-toluene diisocyanate. Among these, hexamethylene diisocyanate represented by formula (4) below is preferable.

In the case of producing a polyurethane by polyaddition of the (a) hydrogenated polybutadiene having isocyanate groups at the terminals and the (b) glycol represented by HO—$R_3$—OH (wherein $R_3$ represents a linear or branched C2 to C6 alkylene group optionally having an ether bond) in the aforementioned composition 1, it is more preferable that molar ratio (a):(b)=2:3 to 3:2 be satisfied. When the hydrogenated polybutene portion, which is the hydrophobic part in the molecule of the polyurethane polymer, is large, the solubility in the oil agent increases, and the transparency is improved. Meanwhile, when the amount of the glycol represented by HO—$R_3$—OH (wherein $R_3$ represents a linear or branched C2 to C6 alkylene group optionally having an ether bond), which constitutes the hydrophilic part in the molecule of the polyurethane polymer, is large, the self-association of the polyurethane gel is enhanced, and the elasticity increases, but the solubility decreases. That is, the balance between the hydrophobic part and the hydrophilic part is important, and a suitable molar ratio thereof is 2:3 to 3:2. Examples of the molar ratio (a):(b) that falls within such a range include 2:3 to 3:2, 3:4 to 4:3, 4:5 to 5:4, 4:5 to 4:3, and 9:10 to 10:9. In this case, the (a) preferably has an average molecular weight (Mw) of 1000 to 3000. Examples of the molecular weight that falls within such a range include 1200 to 2800, 1200 to 2600, 1200 to 2400, 1200 to 2000, 1200 to 1800, 1300 to 2700, 1300 to 2500, 1300 to 2100, 1300 to 1800, 1500 to 2500, 1500 to 2100, 1800 to 2800, 1800 to 2600, 1800 to 2400, and 1800 to 2100, other than 1000 to 3000.

In the case of producing a polyurethane by polyaddition of the (c) hydrogenated polybutadiene having hydroxyl groups at the terminals, the (d) diisocyanate compound, and the (b) glycol represented by HO—$R_3$—OH (wherein $R_3$ represents a linear or branched C2 to C6 alkylene group optionally having an ether bond) in the aforementioned composition 2, it is more preferable that molar ratio (c):(b) =2:3 to 3:2 be satisfied. When the hydrogenated polybutene portion, which is the hydrophobic part in the molecule of the polyurethane polymer, is large, the solubility in the oil agent increases, and the transparency is improved. Meanwhile, when the amount of the glycol represented by HO—$R_3$—OH (wherein $R_3$ represents a linear or branched C2 to C6 alkylene group optionally having an ether bond), which constitutes the hydrophilic part in the molecule of the polyurethane polymer, is large, the self-association of the polyurethane gel increases, and the elasticity increases, but the solubility decreases. That is, the balance between the hydrophobic part and the hydrophilic part is important, and a suitable molar ratio thereof is 2:3 to 3:2. Examples of the molar ratio (c):(b) that falls within such a range include 2:3 to 3:2, 3:4 to 4:3, 4:5 to 5:4, 4:5 to 4:3, and 9:10 to 10:9. In this case, the (c) preferably has an average molecular weight (Mw) of 1000 to 3000. Examples of the molecular weight that falls within such a range include 1200 to 2800, 1200 to 2600, 1200 to 2400, 1200 to 2000, 1200 to 1800, 1300 to 2700, 1300 to 2500, 1300 to 2100, 1300 to 1800, 1500 to 2500, 1500 to 2100, 1800 to 2800, 1800 to 2600, 1800 to 2400, and 1800 to 2100, other than 1000 to 3000.

Further, the polyurethane obtained by the polyaddition preferably has an average molecular weight (Mw) of 10000 to 100000. Examples of the molecular weight that falls within such a range include 10000 to 100000, 10000 to 90000, 10000 to 80000, 10000 to 70000, 10000 to 60000, 10000 to 50000, 20000 to 90000, 20000 to 80000, 20000 to 70000, 20000 to 60000, 20000 to 50000, 30000 to 90000, 30000 to 80000, 30000 to 70000, 30000 to 60000, 30000 to 50000, 40000 to 90000, 40000 to 80000, 40000 to 70000, 40000 to 60000, 50000 to 90000, 50000 to 80000, and 50000 to 70000.

It is more preferable that the polyurethane represented by A used in the present invention be oil soluble. In the present invention, to be "oil soluble" means to be "dissolvable in cetyl 2-ethylhexanoate at 30° C. in an amount of at least 1 mass % or more".

It is more preferable that the polyurethane represented by A be contained in Composition 1 in an amount of 1 to 35 mass %. In the case where the concentration of the polyurethane polymer falls below this range, the transparency is high, but the elastic feeling (load) is poor, and the resilient feeling given to cosmetics is poor. Examples of the content of the polyurethane that falls within such a range include 1 to 35 mass %, 1 to 30 mass %, 1 to 25 mass %, 1 to 20 mass %, 1 to 15 mass %, 1 to 10 mass %, 1 to 5 mass %, 5 to 30 mass %, 5 to 25 mass %, 5 to 20 mass %, 5 to 15 mass %, 5 to 10 mass %, 10 to 30 mass %, 10 to 25 mass %, 10 to 20 mass %, and 10 to mass %. Further, the oil agent represented by B is preferably contained in Composition 1 in an amount of 65 to 99 mass %. Examples of the content of the oil agent that falls within such a range include 65 to 99 mass %, 70 to 99 mass %, 80 to 99 mass %, 85 to 99 mass %, 90 to 99 mass %, 95 to 99 mass %, 70 to 95 mass %, 75 to 95 mass %, 80 to 95 mass %, 85 to 95 mass %, 90 to 95 mass %, 70 to 90 mass %, 75 to 90 mass %, 80 to 90 mass %, and 85 to 90 mass %.

It is more preferable that the polyurethane represented by A be contained in Composition 2 in an amount of 1 to 35 mass %. In the case where the concentration of the polyurethane polymer falls below this range, the transparency is high, but the elastic feeling (load) is poor, and the resilient feeling given to cosmetics is poor. Examples of the content of the polyurethane that falls within such a range include 1 to 35 mass %, 1 to 30 mass %, 1 to 25 mass %, 1 to 20 mass %, 1 to 15 mass %, 1 to 10 mass %, 1 to 5 mass %, 5 to 30 mass %, 5 to 25 mass %, 5 to 20 mass %, 5 to 15 mass %, 5 to 10 mass %, 10 to 30 mass %, 10 to 25 mass %, 10 to 20 mass %, and 10 to mass %. Further, the oil agent represented by B is preferably contained in Composition 2 in an amount of 65 to 99 mass %. Examples of the content of the oil agent that falls within such a range include 65 to 99 mass %, 70 to 99 mass %, 80 to 99 mass %, 85 to 99 mass %, 90 to 99 mass %, 95 to 99 mass %, 70 to 95 mass %, 75 to 95 mass %, 80 to 95 mass %, 85 to 95 mass %, 90 to 95 mass %, 70 to 90 mass %, 75 to 90 mass %, 80 to 90 mass %, and 85 to 90 mass %.

The oil agent represented by B used in the polyurethane gel composition is not specifically limited, as long as it is generally used for cosmetics. The properties are not specifically limited, but the oil agent is preferably in liquid form at 10° C. to 30° C., particularly 25° C.

The origin of the oil agent represented by B to be used in the polyurethane gel composition, such as animal oil, vegetable oil, and synthetic oil, does not matter, and examples thereof include hydrocarbon oil, ester oil, fats and oils, silicone oil, and fluorine oil. Among these, since a lower polarity tends to lead to a higher strength of the polyurethane gel composition, use of one or more selected from hydrocarbon oil, ester oil having 0 or 1 hydroxyl group, and silicone oil containing a phenyl group is shown as an example. Specifically, examples thereof include hydrocarbons such as liquid paraffin, squalane, polybutene, and polyisobutylene, fats and oils such as olive oil, castor oil, mink oil, macadamian nut oil, and jojoba oil, esters such as cetyl isooctanoate (cetyl 2-ethylhexanoate), isopropyl myristate, isopropyl palmitate, octyldodecyl myristate, glyceryl trioctanoate, polyglyceryl diisostearate, diglyceryl isostearate, diisostearyl malate, glyceryl tribehenate, pentaerythrityl rosinate ester, and neopentyl glycol dioctanoate, and silicones such as methylphenylpolysiloxane and diphenylpolysiloxane, and one or more of them can be used.

The polyurethane gel composition of the present invention suitably has exceptionally high elasticity and exceptionally high resilience, in addition to transparency and gloss. As a result of measuring the load by needle penetration, a gel obtained by dissolving 30 parts of the polyurethane gel composition and 70 parts of liquid paraffin (with a dynamic viscosity by the ASTM D445 measurement method at 40° C. of 8 mm$^2$/s) by heating at 85° C., followed by cooling to 30° C., exhibited excellent characteristics, that is, a load of 0.20 to 10.00 N when a needle with a 2-cm-diameter spherical adapter was allowed to penetrate 10 mm at 2 cm/min. This indicates that the polyurethane gel composition of the present invention has an elasticity and a resilience. Further, as to the transparency, the polyurethane gel composition of the present invention has a transmittance at a wavelength of 700 nm of 90% or more. That is, the polyurethane gel composition of the present invention has exceptionally high transparency.

The polyurethane gel Composition 1 of the present invention can be produced using a known method for producing polyurethane. That is, the polyurethane gel Composition 1 of the present invention is obtained by polyaddition reaction by adding the (a) hydrogenated polybutadiene having isocyanate groups at the terminals and the (b) glycol represented by HO—R$_3$—OH (wherein R$_3$ represents a linear or branched C2 to C6 alkylene group optionally having an ether bond), which serve as A, into the oil agent represented by B.

The polyurethane gel Composition 2 of the present invention can be produced using a known method for producing polyurethane. That is, the polyurethane gel Composition 2 of the invention can be produced by introducing the (c) hydrogenated polybutadiene having hydroxyl groups at the terminals, the (b) glycol represented by HO—R$_3$—OH (wherein R$_3$ represents a linear or branched C2 to C6 alkylene group optionally having an ether bond), and the oil agent represented by B, uniformly mixing the mixture, and introducing the (d) diisocyanate compound therein to allow reaction.

As an example of the polyurethanes in the polyurethane gel Composition 1 and the polyurethane gel Composition 2 of the present invention, a polyurethane named "Hydrogenated Polybutadiene/Glycol/HDI Copolymer" in INCI (International Nomenclature of Cosmetic Ingredient) is mentioned.

In the polyurethane gel composition of the present invention, various components that can be contained can be appropriately used, as required. Examples of such components include a volatile component, a surfactant, an oil agent, powder, an aqueous component, alcohols, a water-soluble polymer, an ultraviolet absorber, a humectant, a gelling agent, a thickener, an anti-fading agent, an antioxidant, a defoamer, a cosmetic component (such as a whitening agent, a cell activator, an anti-inflammatory agent, a blood circulation promoter, a skin astringent, and an antiseborrheic agent), a preservative, an antibacterial agent, a flavor, vitamins, amino acids, a nucleic acid, and a hormone.

The aqueous component is not particularly limited, and any aqueous component can be used as long as it is a component in liquid form at normal temperature and is generally used for cosmetics. Examples thereof include water, ethanol, polyhydric alcohols such as propylene glycol, 1,3-butylene glycol, and dipropylene glycol, glycerols such as glycerin, diglycerol, and polyglycerin, and an extract of a plant such as Aloe vera, Hamamelis, cucumber, lemon, lavender, and rose, and one or more of these aqueous components can be used, as needed. The content of such aqueous components used in the present invention differs depending on the usability, the sensation upon application, and the dosage form and is not particularly limited but is preferably 10 mass % or less, further 5 mass % or less, particularly 0.1 mass % in the composition, in view of the cosmetic effect, the usability, and the sensation upon application.

The surfactant is not particularly limited, as long as it is generally used for cosmetics, and any surfactant can be used. Examples of the surfactant include an anionic surfactant, a cationic surfactant, a nonionic surfactant, and an amphoteric surfactant, and one or more of these can be used in combination, as required.

Specifically, examples of the anionic surfactant include a surfactant based on: fatty acid soap such as sodium stearate and triethanolamine palmitate, carboxylate such as alkyl ether carboxylic acid and a salt thereof, and a condensate of amino acid and fatty acid, alkylsulfonic acid, alkene sulfonate, fatty acid ester sulfonate, fatty acid amide sulfonate, alkyl sulfonate and sulfonate of a formalin condensate thereof, sulfate ester salts such as alkyl sulfate ester salt, secondary higher alcohol sulfate ester salt, alkyl and allyl ether sulfate ester salts, fatty acid ester sulfate ester salt, sulfate ester salt of fatty acid alkylol amide, polyoxyethylene alkyl sulfate ester salt, and funnel oil, alkyl phosphate, ether phosphate, alkyl allyl ether phosphate, amide phosphate, N-acyl amino acid, or the like.

Examples of the cationic surfactant include alkyl quaternary ammonium salt or aromatic quaternary ammonium salt such as long-chain alkyltrimethylammonium salt, di-long-chain alkyldimethylammonium salt, long-chain alkyldimethylbenzyl ammonium salt, dipolyoxyethylene alkylmethylammonium salt, dipolyoxyethylene alkyl etherdimethylammonium salt, and polyoxypropylenemethyldiethyl ammonium salt, pyridinium salt such as alkyl pyridinium salt, imidazoline salt such as alkyl dihydroxyethylimidazoline salt, N-acyl basic amino acid lower alkyl ester salt, and amine salt such as alkylamine salt, polyamine, and amino alcohol fatty acid derivative.

Examples of the nonionic surfactant include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkyl phenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene-hardened castor oil, polyoxyethylene-hardened castor oil fatty acid ester, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene-alkyl-co-modified organopolysiloxane, alkanol amide, sugar ether, and sugar amide.

Examples of the amphoteric surfactant include a carbobetaine-type amphoteric surfactant such as alkyldimethylaminoacetic acid betaine, fatty acid amidopropyldimethylaminoacetic acid betaine, and alkyldihydroxyethylaminoacetic acid betaine, a sulfobetaine-type amphoteric surfactant such as alkyl sulfobetaine, an amidoamine-type (imidazoline-type) amphoteric surfactant such as N-fatty acid acyl-N-carboxymethyl-N-hydroxyethyl ethylenediamine salt and N-fatty acid acyl-N-carboxymethoxyethyl-N-carboxymethylethylenediamine disalt, an amino acid-type amphoteric surfactant such as N-[3-alkyloxy-2-hydroxypropyl]arginine salt, and an alkyliminodicarboxylate-type amphoteric surfactant.

Examples of the humectant include urea, hyaluronic acid, chondroitin sulfate, and pyrrolidone carboxylate.

Among examples of the gelling agent, aqueous examples include a plant polymer such as arabic gum, tragacanth gum, galactan, carob gum, guar gum, karaya gum, carrageenan, pectin, agar, quince seed (marmelo), starch (rice, corn, potato, and wheat), algae colloid, trant gum, and locust bean gum, a microbial polymer such as xanthan gum, dextran, succinoglucan, and pullulan, an animal polymer such as collagen, casein, albumin, and gelatin, a starch polymer such as carboxymethyl starch and methylhydroxypropyl starch, a cellulose polymer such as methylcellulose, hydroxypropylmethylcellulose, carboxymethylcellulose, hydroxymethylcellulose, hydroxypropylcellulose, sodium sulfate cellulose, and sodium carboxymethylcellulose, an alginate polymer such as sodium alginate and propylene glycol alginate ester, sodium polyacrylate, carboxyvinyl polymer, alkyl-modified carboxyvinyl polymer, polyacrylamide, a vinyl polymer such as polyvinyl alcohol and polyvinylpyrrolidone, polyethylene glycol, an ethylene oxide-propylene oxide copolymer, an acrylic polymer such as an acrylic acid-sodium acryloyldimethyl taurate copolymer, sodium polyacrylate, polyethyl acrylate, and polyacrylamide, an inorganic gelling agent and a thickener such as bentonite, magnesium aluminum silicate, laponite, hectorite, and anhydrous silicic acid, polyethyleneimine, and a cation polymer.

As a film forming agent, natural rubber, natural cellulose, cationized cellulose, various acrylic resins (including a copolymer), various alkyd resins, polyvinyl alcohol, polyvinylpyrrolidone, nitro cellulose, various silicone resins (including a copolymer), urea resin, modified corn starch, and the like are used. Specifically, examples of the film forming agent include an acrylic acid amide-alkyl acrylate-methoxypolyethylene glycol methacrylate copolymer, methoxypolyethylene glycol methacrylate, an eicosene-vinylpyrrolidone polymer, a 1,1'-methylenebis (4-isocyanatocyclohexane)polypropylene glycol copolymer, perfluoropolyether, an (acrylate/polytrimethylsiloxymethacrylate) copolymer, polypropylsilsesquioxane, an (eicosene/vinylpyrrolidone) copolymer, a (vinylpyrrolidone/hexadecene) copolymer, hydroxyethyl cellulose, and silicone-modified norbornene.

A coloring agent is not specifically limited by the shape such as a spherical shape, a plate shape, a spindle shape, and a needle shape, the particle size such as fumy particles, fine particles, and a pigment level, or the particle structure such as a porous or non-porous structure, as long as the coloring agent is generally used for cosmetics, and an inorganic pigment, an organic pigment, a bright pigment, a metal or the like can be used. Specifically, examples of the powder can include a white inorganic pigment such as titanium oxide, zinc oxide, cerium oxide, and barium sulfate, a colored inorganic pigment such as iron oxide, carbon black, chromium oxide, chromium hydroxide, iron blue, ultramarine, and colcothar, a bright pigment such as titanium mica, bismuth oxychloride, organic pigment-treated titanium mica, titanium dioxide-coated mica, titanium dioxide-coated synthetic phlogopite, titanium dioxide-coated bismuth oxychloride, iron oxide mica titanium, prussian blue-treated mica titanium, carmine-treated mica titanium, a fish scale, titanium dioxide-coated glass powder, resin laminate powder including polyethylene terephthalate-aluminum-epoxy laminate powder, polyethylene terephthalate-polyolefin laminate film powder, and polyethylene terephthalate-polymethylmethacrylate laminate film powder, organic pigment powder such as Red No. 201, Red No. 202, Red No. 205, Red No. 226, Red No. 228, Orange No. 203, Orange No. 204, Blue No. 404, and Yellow No. 401, organic pigment powder of zirconium, barium, or aluminum lake such as Red No. 3, Red No. 104, Red No. 106, Orange No. 205, Yellow No. 4, Yellow No. 5, Green No. 3, and Blue No. 1, metal powder such as aluminum powder, gold powder, and silver powder, and composite powder such as fine particle titanium oxide-coated mica titanium, fine particle zinc oxide-coated titanium mica, barium sulfate-coated titanium mica, titanium oxide-containing silicon dioxide, and zinc oxide-containing silicon dioxide. Examples of a natural dye include carmine, laccaic acid, carthamin, brazilin, and crocin. One or more types of these can be used, as required. These may be subjected to surface treatment using one or more of a fluorine-containing compound, a silicone compound, metal soap, lecithin, hydrogenated lecithin, collagen, hydrocarbon, higher fatty acid, higher alcohol, ester, wax, a surfactant, and the like.

Powder other than the coloring agent is not specifically limited by the shape such as a plate shape, a spindle shape, and a needle shape, the particle size such as fumy particles and a pigment level, and the particle structure such as a porous or non-porous structure, as long as it is generally used as a raw material for cosmetics, and examples thereof include inorganic powders such as aluminum oxide, cerium oxide, magnesium oxide, zirconium oxide, magnesium carbonate, calcium carbonate, aluminum silicate, magnesium silicate, magnesium aluminum silicate, mica, synthetic mica, synthetic sericite, sericite, talc, kaolin, silica, silicon carbide, and boron nitride, and organic powders such as magnesium stearate, zinc stearate, N-acyllidine, and nylon. One or more types of these can be used. Further, one or more of such powder may be compounded for use, and the surface thereof may be treated with an oil agent, a silicone compound, a water-soluble polymer, or the like.

Examples of the oil agent include solid oil, semi-solid oil, and liquid oil and further include natural animal and vegetable oil, semi-synthetic oil, hydrocarbon oil, ester oil, glyceride oil, silicone oil, higher alcohol, higher fatty acid, and an organic solvent.

Examples of the solid oil can include natural wax such as carnaubaro, candelilla wax, cotton wax, shellac wax, and hardened oil, mineral wax such as ozokerite, ceresin, paraffin wax, and microcrystalline wax, synthetic wax such as polyethylene wax, Fischer-Tropsch wax, and an ethylene-propylene copolymer, higher alcohol such as behenyl alcohol, cetyl alcohol, stearyl alcohol, cholesterol, and phytosterol, and higher fatty acid such as stearic acid and behenic acid.

Specifically, examples of the natural animal and vegetable oil and the semi-synthetic oil that are liquid include avocado oil, linseed oil, almond oil, Ericerus pela wax, perilla oil, olive oil, kaya (Torreya nucifera) oil, liver oil, apricot kernel oil, wheat germ oil, sesame oil, rice germ oil, rice bran oil, sasanqua oil, safflower oil, Chinese tung oil, cinnamon oil, turtle oil, soybean oil, tea seed oil, camellia oil, evening primrose oil, corn oil, rapeseed oil, Japanese tung oil, rice bran wax, germ oil, persic oil, palm oil, palm kernel oil, castor oil, sunflower oil, grape oil, jojoba oil, macadamia nut oil, cottonseed oil, coconut oil, tri-coconut oil fatty acid glyceride, peanuts oil, lanolin, liquid lanolin, reduced lanolin, lanolin alcohol, lanolin acetate, lanolin fatty acid isopropyl, POE lanolin alcohol ether, POE lanolin alcohol acetate, lanolin fatty acid polyethylene glycol, POE hydrogenation lanolin alcohol ether, and egg yolk oil.

Examples of the hydrocarbon oil include squalane, squalene, liquid paraffin, pristane, and polyisobutylene.

Examples of the ester oil include diisobutyl adipate, 2-hexyldecyl adipate, di-2-heptyl undecyl adipate, N-alkylglycol monoisostearate, isocetyl isostearate, trimethylolpropane triisostearate, cetyl 2-ethylhexanoate, ethylene glycol di-2-ethylhexanoate, neopentyl glycol di-2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, 2-octyldodecyl myristate, 2-hexyldecyl myristate, myristyl myristate, hexyldecyldimethyl octanoate, ethyl laurate, hexyl laurate, N-lauroyl-L-glutamic acid-2-octyl dodecyl ester, and diisostearyl malate.

Examples of the glyceride oil include acetoglyceride, glyceride triisooctanoate, glyceride triisostearate, glyceride triisopalmitate, glyceride tri-2-ethylhexanoate, glyceride monostearate, glyceride di-2-heptylundecanoate, and glyceride trimyristate.

Examples of the silicone oil include dimethylpolysiloxane, methylphenylpolysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane, and alkyl-modified silicone.

Examples of the higher alcohol include oleyl alcohol, lauryl alcohol, stearyl alcohol, isostearyl alcohol, and 2-octyl dodecanol.

Examples of the higher fatty acid include oleic acid, palmitic acid, myristic acid, stearic acid, and isostearic acid.

Examples of the organic solvent include hydrocarbon such as n-hexane and cyclohexane, an aromatic compound such as benzene, toluene, and xylene, a non-aromatic compound such as ethyl acetate and butyl acetate, a chlorine compound such as chloroform, dichloromethane, and dichloroethane, an ether compound such as dioxane and tetrahydrofuran, 2-propanol, benzyl alcohol, phenoxyethanol, carbitols, cellosolves, and spindle oil.

Specifically, examples of the alcohols include lower alcohol such as ethanol and isopropanol, polyhydric alcohol such as glycerin, diglycerol, polyglycerin, diethylene glycol, polyethylene glycol, propylene glycol, dipropylene glycol, polypropylene glycol, 1,3-butylene glycol, and erythritol, sugar alcohol such as sorbitol, maltose, xylitol, and maltitol, and benzyl alcohol.

Examples of the cosmetic components include a whitening agent such as arbutin, glutathione, and a saxifrage extract, a cell activator such as royal jelly, a photosensitizer, cholesterol derivative, and a calf blood extract, a rough-skin improving agent, a blood circulation promoter such as nonylic acid vanillyl amide (4-hydroxy-3-methoxybenzyl nonylic acid amide), nicotinic acid benzyl ester, nicotinic acid β-butoxyethyl ester, capsaicin, zingerone, cantharides tincture, ichthammol, caffeine, tannic acid, α-borneol, tocopherol nicotinate, inositol hexanicotinate, cyclandelate, cinnarizine, tolazoline, acetyl choline, verapamil, cepharanthine, and γ-orizanol, a skin astringent such as zinc oxide and tannic acid, and an antiseborrheic agent such as sulfur and thianthol.

Examples of the preservative and the antibacterial agent include paraoxybenzoic acid ester, benzoic acid, sodium benzoate, sorbic acid, potassium sorbate, phenoxyethanol, salicylic acid, coal acid, parachlorometacresol, hexachlorophene, benzalkonium chloride, chlorhexidine chloride, trichlorocarbanilide, a photosensitizer, and isopropylmethylphenol.

Examples of the flavor include a natural flavor (an animal flavor and a vegetable flavor), a synthetic flavor, and a prepared flavor (blend of a natural flavor and a synthetic flavor), and a prepared flavor blending a natural flavor and a synthetic flavor is most commonly used currently for cosmetics. Examples of the flavor include jasmine, Tagetes minuta, rosemary, vanilla, ginger oil, rose oil, jasmine oil, lavender oil, ylang-ylang oil, peppermint oil, geranium oil, lemon oil, orange oil, star anise oil, grapefruit oil, Eucalyptus oil, sandalwood oil, black pepper oil, basil oil, ylang-ylang oil, patchouli oil, coumarin, musk ketone, heliotropin, 1-octen-3-ol, and a blend of these.

Examples of the antioxidant include tocopherol, butylhydroxyanisole, and dibutylhydroxytoluene, examples of the pH adjuster include lactic acid, lactate, citric acid, citrate, glycolic acid, succinic acid, tartaric acid, malic acid, potassium carbonate, sodium bicarbonate, and ammonium bicarbonate, examples of the chelating agent include alanine, sodium edetate, sodium polyphosphate, sodium metaphosphate, phosphate, and hydroxyethane diphosphonic acid, examples of the refreshing agent include L-menthol, camphor, mentha oil, peppermint oil, and Eucalyptus oil, and examples of the anti-inflammatory agent include allantoin, glycyrrhetinic acid salt, glycyrrhetinic derivative, tranexamic acid, and azulene.

Examples of the vitamins include vitamin A such as vitamin A oil, retinol, retinol acetate, and retinol palmitate, vitamin B2 such as riboflavin, riboflavin butyrate, and flavin adenine nucleotide, vitamin B6 such as pyridoxine hydrochloride and pyridoxine dioctanoate, vitamin C such as L-ascorbic acid, L-ascorbic acid dipalmitate ester, sodium L-ascorbic acid-2-sulfate, and dl-α-tocopherol-L-ascorbic acid phosphate diester dipotassium, pantothenic acids such as calcium pantothenate, D-pantothenyl alcohol, pantothenyl ethyl ether, and acetyl pantothenyl ethyl ether, vitamin D such as ergocalciferol and cholecalciferol, nicotinic acids such as nicotinic acid, benzyl nicotinate, and nicotinic acid amide, vitamin E such as dl-α-tocopherol, dl-α-tocopherol acetate, dl-α-tocopherol nicotinate, and dl-α-tocopherol succinate, vitamin P, and biotin.

Examples of the amino acids include arginine, aspartic acid, cystine, cysteine, methionine, serine, leucine, isoleucine, tryptophan, alanine, glycine, and proline, examples of the nucleic acid include deoxyribonucleic acid, and examples of the hormone include estradiol and ethynyl estradiol.

Surfaces of powder can be coated with the polyurethane gel composition of the present invention serving as a surface-treating agent to produce surface-treated powder (which will be hereinafter referred to as "polyurethane gel-treated powder"). The powder to be coated with the polyurethane gel composition of the present invention is not specifically limited by the shape such as a spherical shape, a plate shape, and a needle shape, the particle size such as fumy particles, fine particles, and a pigment level, or the particle structure such as a porous or non-porous structure, as long as it is powder generally used for cosmetics, and one or more of inorganic powders, bright powders, organic powders, dye powders, and composite powders can be used.

As the inorganic powders, one or more selected from titanium oxide, black titanium oxide, Prussian blue, ultramarine, colcothar, yellow iron oxide, black iron oxide, zinc oxide, aluminum oxide, silica, magnesium oxide, zirconium oxide, magnesium carbonate, calcium carbonate, chromium oxide, chromium hydroxide, carbon black, aluminum silicate, magnesium silicate, magnesium aluminum silicate, mica, synthetic mica, sericite, talc, kaolin, silicon carbide, barium sulfate, bentonite, smectite, boron nitride, and the like can be used. These may be prepared as fine particles of about 10 to 100 nm for use.

As the bright powders, one or more selected from bismuth oxychloride, titanium oxide-coated mica, iron oxide-coated mica, iron oxide-coated mica titanium, organic pigment-coated mica titanium, titanium oxide-coated glass powder, aluminum powder, and the like can be used.

As the organic powders, one or more selected from nylon powder, polymethylmethacrylate powder, acrylonitrile-methacrylic acid copolymer powder, vinylidene chloride-methacrylic acid copolymer powder, PET resin powder, polyethylene powder, polystyrene powder, organopolysiloxane elastomer powder, polymethylsilsesquioxane powder, polyurethane powder, wool powder, silk powder, crystalline cellulose powder, N-acyllidine powder, and the like can be used.

As the dye powders, one or more selected from an organic tar pigment, a lake pigment of an organic dye, and the like can be used.

As the composite powders, one or more selected from fine particle titanium oxide-coated mica titanium, fine particle zinc oxide-coated mica titanium, barium sulfate-coated mica titanium, titanium oxide-containing silica, zinc oxide-containing silica, and the like can be used.

Among these, titanium oxide, colcothar, talc, sericite, and mica, which are inorganic powder, are particularly suitable as the powder to be coated. Such powder is widely used in cosmetics and contained in a large amount, and thus can exert a remarkable effect by the coating treatment when used in cosmetics.

The method for coating such powder with the aforementioned polyurethane gel is not specifically limited, and the production is performed by a generally known method. Examples thereof include a method of directly mixing the polyurethane gel with the powder (dry treatment method) and a method using a solvent (wet method). Among these, a wet method of kneading a dispersion obtained by dispersing the polyurethane gel in a solvent with the powder and thereafter removing the solvent by evaporation, followed by completely drying, is preferable for obtaining polyurethane gel-treated powder that is uniform and has excellent sensation upon application. By further pulverizing this, polyurethane gel-treated powder that is more uniform and has more excellent sensation upon application can be produced. The pulverization method is also not specifically limited. The compound to be used as the solvent is not specifically limited, as long as the polyurethane gel can be dispersed therein, but examples thereof can include water, ethanol, n-propyl alcohol, isopropyl alcohol, n-hexane, isoparaffin, benzene, and toluene, and one or more thereof can be used. For obtaining polyurethane gel-treated powder that is more uniform and has more excellent sensation upon application, one or more of isopropyl alcohol and n-hexane is preferably used.

Further, the polyurethane gel-treated powder may be further coated with a generally known surface-treating agent such as a silicone compound, a fluorine compound, an oil agent, fats and oils, a higher alcohol, a wax, a polymer, and a resin, in order to improve the dispersibility in a cosmetic base and the texture.

The polyurethane gel-treated powder is formed by treating the powder surface with the polyurethane gel, and the polyurethane gel is present on the powder surface. The coating amount is not specifically limited but is preferably 0.1 to 10 mass % with reference to the total mass of the coated powder, for further remarkably exerting the effects of the present invention. Examples of the coating amount that falls within such a range include 0.1 to 10 mass %, 0.1 to 7.5 mass %, 0.1 to 5 mass %, 0.5 to 10 mass %, 0.5 to 7.5 mass %, 0.5 to 5 mass %, 1 to 10 mass %, 1 to 7.5 mass %, 1 to 5 mass %, 2 to 10 mass %, 2 to 7.5 mass %, 2 to 5 mass %, 3 to 10 mass %, 3 to 7.5 mass %, and 3 to 5 mass %.

A cosmetic can be produced according to a conventional method using one or more of such polyurethane gel-treated powder described above in combination with known cosmetic components. The content of the treated powder in the aforementioned cosmetic is not specifically limited and differs depending on the dosage form of the cosmetic but is 1 to 99 mass %, preferably 5 to 95 mass %. Further, the cosmetic using the polyurethane gel-treated powder can exert a remarkable effect in the case of being a powder cosmetic containing the powder as a main component. In such a case, the content is preferably 1 to 70 mass %, further 5 to 50 mass %, particularly 10 to 30 mass %.

Components that can be contained can be appropriately used, as required, for the cosmetic containing the polyurethane gel-treated powder.

For example, other components that are generally used for cosmetics in order to impart various effects, such as the volatile component, the surfactant, the oil agent, the powder, the aqueous component, the alcohols, the water-soluble polymer, the ultraviolet absorber, the humectant, the gelling agent, the thickener, the anti-fading agent, the antioxidant, the defoamer, the cosmetic components (such as the whitening agent, the cell activator, the anti-inflammatory agent, the blood circulation promoter, the skin astringent, and the antiseborrheic agent), the preservative, the antibacterial agent, the flavor, the vitamins, the amino acids, the nucleic acid, and the hormone, which are described above, can be appropriately used.

The cosmetic can be produced according to a conventional method using the polyurethane gel composition of the present invention in combination with known cosmetic components. In the cosmetic, the content of the polyurethane gel composition is not specifically limited and differs depending on the dosage form of the cosmetic but is 0.1 to 99 mass %, preferably 1 to 95 mass %.

Components that can be contained can be appropriately used in the cosmetic containing the polyurethane gel composition, as required.

Examples of such components include the volatile component, the surfactant, the oil agent, the powder, the aqueous component, the alcohols, the water-soluble polymer, the ultraviolet absorber, the humectant, the gelling agent, the thickener, the anti-fading agent, the antioxidant, the defoamer, the cosmetic components (such as the whitening agent, the cell activator, the anti-inflammatory agent, the blood circulation promoter, the skin astringent, and the antiseborrheic agent), the preservative, the antibacterial agent, the flavor, the vitamins, the amino acids, the nucleic acid, and the hormone, which are described above.

The polyurethane gel composition of the present invention can be used for producing cosmetics in various dosage forms such as liquid form, milky lotion form, cream form, solid form, paste form, gel form, powder form, pressed form, multilayered form, mousse form, spray form, or stick form. Further, the polyurethane gel composition of the present invention can be used for producing cosmetics targeting various application sites, such as a makeup cosmetic, a skin care cosmetic, a hair cosmetic, an antiperspirant, or a cosmetic for UV protection.

Examples of a cosmetic item containing the polyurethane gel composition of the present invention include a basic cosmetic such as a skin lotion, a milky lotion, a beauty essence, a pack, an all-in-one gel, a cream, a body milk, an oil cleansing, a cleansing cream, and a sunscreen, a hair cosmetic such as a styling water and a hair wax, a makeup cosmetic such as a mascara, a lip gloss, a lipstick, an eye shadow, an eyeliner, a foundation, a face color, a concealer, and a makeup base.

Hereinafter, the present invention will be described further in detail by way of examples. The present invention is not limited by these examples at all.

All of Production Examples 1 to 5 below relate to Composition 2. However, a polyurethane gel can be produced in the same manner also in the case of using Composition 1 by replacing the terminally hydroxylated polybutadiene with hydrogenated polybutadiene having isocyanate groups at the terminals.

Specifically, the procedure is as follows. That is, the polyurethane in Composition 2 is a polyurethane obtained by reaction of the (c) hydrogenated polybutadiene having hydroxyl groups at the terminals, the (d) diisocyanate compound, and the (b) glycol represented by HO—$R_3$—OH (wherein $R_3$ represents a linear or branched C2 to C6 alkylene group optionally having an ether bond). In contrast, the polyurethane in Composition 1 is a polyurethane obtained by reaction of the (a) hydrogenated polybutadiene and the glycol represented by HO—$R_3$—OH (wherein $R_3$ represents a linear or branched C2 to C6 alkylene group optionally having an ether bond), with the (c) hydrogenated polybutadiene having hydroxyl groups at the terminals in Composition 2 replaced with the (a) hydrogenated polybutadiene having isocyanate groups at the terminals. In this case, similar polyurethanes can be produced by setting the molar ratio of (a) to (b) equal to the molar ratio of (c) to (b).

EXAMPLES

Production Example 1

899 parts of terminally hydroxylated polybutadiene (molecular weight: 2200), 2450 parts of cetyl 2-ethylhexanoate, and 128 parts of hexamethylene diisocyanate were added into a 3-L three-necked flask and were uniformly mixed.

0.9 parts of dibutyltin dilaurate was introduced therein under control at 60° C., followed by stirring for 3 hours, and 24 parts of ethylene glycol was then introduced therein.

After the completion of the introduction, the mixture was stirred at 80° C. for 5 hours, and 18 parts of ethanol was then added thereto to complete the reaction.

The polyurethane in the polyurethane gel obtained had a weight-average molecular weight, as measured by GPC (in terms of polystyrene), of 10000. Further, a gel obtained by dissolving 30 parts of the gel obtained in 70 parts of liquid paraffin by heating at 85° C., followed by cooling to 30° C., had a load, as measured using a load measuring machine (available from Rheotech Co., Ltd.) by allowing a needle with a 2-cm-diameter spherical adapter to penetrate 10 mm at 2 cm/min, of 2.50 N.

Production Example 2

899 parts of terminally hydroxylated polybutadiene (molecular weight: 2200), 2450 parts of cetyl 2-ethylhexanoate, and 128 parts of hexamethylene diisocyanate were added into a 3-L three-necked flask and were uniformly mixed.

0.9 parts of dibutyltin dilaurate was introduced therein under control at 60° C., followed by stirring for 3 hours, and 24 parts of ethylene glycol was then introduced therein.

After the completion of the introduction, the mixture was stirred at 80° C. for 10 hours, and 18 parts of ethanol was then added therein to complete the reaction.

The polyurethane in the polyurethane gel obtained had a weight-average molecular weight, as measured by GPC (in terms of polystyrene), of 50000. Further, a gel obtained by dissolving 30 parts of the gel obtained in 70 parts of liquid paraffin by heating at 85° C., followed by cooling to 30° C., had a load, as measured using a load measuring machine (available from Rheotech Co., Ltd.) by allowing a needle with a 2-cm-diameter spherical adapter to penetrate 10 mm at 2 cm/min, of 5.00 N.

Production Example 3

899 parts of terminally hydroxylated polybutadiene (molecular weight: 2200), 2450 parts of cetyl 2-ethylhexanoate, and 128 parts of hexamethylene diisocyanate were added into a 3-L three-necked flask and were uniformly mixed.

0.9 parts of dibutyltin dilaurate was introduced therein under control at 60° C., followed by stirring for 3 hours, and 24 parts of ethylene glycol was then introduced therein under dilution with cetyl 2-ethylhexanoate.

After the completion of the introduction, the mixture was stirred at 80° C. for 15 hours, and 18 parts of ethanol was then added therein to complete the reaction.

The polyurethane in the polyurethane gel obtained had a weight-average molecular weight, as measured by GPC (in terms of polystyrene), of 100000. Further, a gel obtained by dissolving 30 parts of the gel obtained in 70 parts of liquid paraffin by heating at 85° C., followed by cooling to 30° C., had a load, as measured using a load measuring machine (available from Rheotech Co., Ltd.) by allowing a needle with a 2-cm-diameter spherical adapter to penetrate 10 mm at 2 cm/min, of 7.50 N.

Production Example 4

899 parts of terminally hydroxylated polybutadiene (molecular weight: 2200), 24 parts of ethylene glycol, 0.9 parts of dibutyltin dilaurate, and 2450 parts of cetyl 2-ethylhexanoate were added into a 3-L three-necked flask and were uniformly mixed.

128 parts of hexaethylene diisocyanate was introduced therein under control at 60° C. After the completion of the introduction, the mixture was stirred at 80° C. for 10 hours, and 18 parts of ethanol was then added therein to complete the reaction.

The polyurethane in the polyurethane gel obtained had a weight-average molecular weight, as measured by GPC (in terms of polystyrene), of 50000. Further, a gel obtained by dissolving 30 parts of the gel obtained in 70 parts of liquid paraffin by heating at 85° C., followed by cooling to 30° C., had a load, as measured using a load measuring machine (available from Rheotech Co., Ltd.) by allowing a needle with a 2-cm-diameter spherical adapter to penetrate 10 mm at 2 cm/min, of 3.00 N.

Production Example 5

899 parts of terminally hydroxylated polybutadiene (molecular weight: 2200), 24 parts of ethylene glycol, 0.9 parts of dibutyltin dilaurate, and 2450 parts of cetyl 2-ethylhexanoate were added into a 3-L three-necked flask and were uniformly mixed.

128 parts of hexaethylene diisocyanate was introduced therein under control at 60° C. After the completion of the introduction, the mixture was stirred at 80° C. for 15 hours, and 18 parts of ethanol was then added therein to complete the reaction.

The polyurethane in the polyurethane gel obtained had a weight-average molecular weight, as measured by GPC (in terms of polystyrene), of 100000. Further, a gel obtained by dissolving 30 parts of the gel obtained in 70 parts of liquid paraffin by heating at 85° C., followed by cooling to 30° C., had a load, as measured using a load measuring machine (available from Rheotech Co., Ltd.) by allowing a needle with a 2-cm-diameter spherical adapter to penetrate 10 mm at 2 cm/min, of 4.50 N.

Production Comparative Example 1

100 parts of crosslinked silicone gel (KSG-43 Shin-Etsu Chemical Co., Ltd.) was used.

Production Comparative Example 2

35 parts of dextrin fatty acid ester (Rheopearl ISK, available from Chiba Flour Milling Co., Ltd.) and 65 parts of cetyl 2-ethylhexanoate were heated at 90° C., followed by cooling, to prepare a polysaccharide gel.

Production Comparative Example 3

35 parts of crystalline polyethylene wax (PERFORMALENE655, available from New Phase Technologies) and 65 parts of cetyl 2-ethylhexanoate were heated at 90° C., followed by cooling, to prepare a wax oil gel.

Experimental Example 1

[Evaluation of Gel]

Out of the polyurethane gels obtained by the aforementioned fabrication methods, the polyurethane gel of Production Example 2 was evaluated for the load of the gel with various oil agents that were widely used for cosmetics and the transparency of the gel. Table 1 shows the results. Further, various evaluation methods were as follows.

TABLE 1

Evaluation of gel composition with various oil agents (mass %)

| No. | Component | Experimental Example 1 | 2 | 3 | 4 | 5 | 6 |
|---|---|---|---|---|---|---|---|
| 1 | Polyurethane gel of Production Example 2 | 30 | 30 | 30 | 30 | 30 | 30 |
| 2 | Polyglyceryl monostearate (note 1) | 70 | — | — | — | — | — |
| 3 | Polyglyceryl distearate (note 2) | — | 70 | — | — | — | — |
| 4 | Polyglyceryl tristearate (note 3) | — | — | 70 | — | — | — |
| 5 | Polyglyceryl tetrastearate (note 4) | — | — | — | 70 | — | — |
| 6 | Cetyl 2-ethyl-hexanoate (note 5) | — | — | — | — | 70 | — |
| 7 | Liquid paraffin | — | — | — | — | — | 70 |
| <Evaluation item> | | | | | | | |
| | Load | 0.05 | 0.10 | 0.56 | 5.70 | 3.50 | 5.00 |
| | Transparency | A | A | A | A | A | A |

(note 1): COSMOL 41V (available from The Nisshin OilliO Group, Ltd.)
(note 2): COSMOL 42V (available from The Nisshin OilliO Group, Ltd.)
(note 3): COSMOL 43V (available from The Nisshin OilliO Group, Ltd.)
(note 4): COSMOL 44V (available from The Nisshin OilliO Group, Ltd.)
(note 5): SALACOS 816T (available from The Nisshin OilliO Group, Ltd.)

[Measurement and Evaluation for Load]

The polyurethane gel of Production Example 2 and each of various oil agents shown in Table 1 were dissolved by heating at 85° C., followed by cooling to 30° C., to prepare an elastic gel. The load of the gel was measured using a load measuring machine (available from Rheotech Co., Ltd.) by allowing a needle with a 2-cm-diameter spherical adapter to penetrate 10 mm at 2 cm/min. From the results of Examples 1 to 4, it was confirmed that oil agents with a smaller number of hydroxyl groups in the molecule tended to have a higher load. This is probably because the hydroxyl groups in such an oil agent affected the hydrophilic moiety in the hydrophilic group-associative thickening mechanism of the polyurethane gel, thereby reducing the viscosity.

[Measurement and Evaluation for Transparency]

For determining the transparency of various gels shown in Table 1, the transmittance at 700 nm was measured using a transmittance measuring instrument (available from SHIMADZU CORPORATION). As a result, the gels of Examples 1 to 6 all showed good transparency (A) of 90% or more.

[Measurement and Evaluation of Self-Resilience]

Using the polyurethane gel of Production Example 2 and the dextrin fatty acid ester gel of Production Comparative Example 2, the self-resilience was evaluated. Each measurement sample was diluted with cetyl 2-ethylhexanoate to a purity of 10.5 mass %, followed by heating at 85° C., and was then poured into a jar container, followed by cooling to 30° C., to prepare an elastic gel. Using a texture analyzer (available from EKO Instruments B.V.), the sample prepared was subjected repeatedly 7 times to the same motion of allowing a needle to penetrate 5 mm at a rate of 1 mm/min from the time when a load of 5 g was applied thereto by a 2-cm-diameter spherical adapter, and it was confirmed whether the gel structure was not broken by the load and thus had a resilience. FIG. 1 shows a schematic diagram of the measurement. As a result (FIG. 2), it turned out that the gel structure of the dextrin fatty acid ester gel of Production Comparative Example 2 was broken by the repeated load and thus did not follow the same curve, whereas the polyurethane gel of Production Example 2 followed the same curve without collapse of the gel due to the repeated load and thus had high resilience of the gel. Further, it turned out that the elasticity was excellent since the value of the load itself was higher than in the dextrin fatty acid ester gel of Production Comparative Example 2.

From the aforementioned studies, it turned out that the polyurethane gel composition of the present invention is a highly novel gel having excellent transparency, high elasticity, and further excellent self-resilience.

Experimental Example 2

[Evaluation of Gel]

The polyurethane gels of Production Examples 6 to 16 were produced as shown in Table 2 in the same manner as in Production Example 2 except that the mixing ratio of the components of terminally hydroxylated polybutadiene, hexamethylene diisocyanate, cetyl 2-ethylhexanoate and ethylene glycol, was changed. The load and the transparency of these polyurethane gels were evaluated. Table 2 shows the results. For reference, Table 2 also shows the data of the polyurethane gel of Production Example 2. The evaluation methods were as follows.

TABLE 2

Evaluation of polyurethane gel composition (parts)

| No. | Component | Production Example 6 | 7 | 8 | 2 | 9 | 10 | 11 | 12 | 13 | 14 | 15 | 16 |
|---|---|---|---|---|---|---|---|---|---|---|---|---|---|
| 1 | (c) Terminally hydroxylated polybutadiene | 899 | 899 | 899 | 899 | 899 | 899 | 899 | 18 | 180 | 360 | 1034 | 1259 |
| 2 | (d) Hexamethylene diisocyanate | 128 | 128 | 128 | 128 | 128 | 128 | 128 | 3 | 26 | 51 | 147 | 179 |
| 3 | Cetyl 2-ethylhexanoate | 2450 | 2450 | 2450 | 2450 | 2450 | 2450 | 2450 | 3480 | 3291 | 3081 | 2292 | 2030 |
| 4 | (b) Ethylene glycol | 12 | 17 | 19 | 24 | 31 | 37 | 44 | 0.48 | 4.8 | 9.6 | 27.6 | 33.6 |
| | Molar ratio (c)/(b) | 2.11 | 1.49 | 1.33 | 1.06 | 0.82 | 0.69 | 0.58 | 1.06 | 1.06 | 1.06 | 1.06 | 1.06 |

TABLE 2-continued

Evaluation of polyurethane gel composition (parts)

| | | Production Example | | | | | | | | | | | |
|---|---|---|---|---|---|---|---|---|---|---|---|---|---|
| No. | Component | 6 | 7 | 8 | 2 | 9 | 10 | 11 | 12 | 13 | 14 | 15 | 16 |
| | Content of A (polyurethane) (mass %) | 29.8 | 29.9 | 29.9 | 30.0 | 30.2 | 30.3 | 30.4 | 0.6 | 6.0 | 12.0 | 34.5 | 42.0 |
| | Content of B (oil agent) (mass %) | 70.2 | 70.1 | 70.1 | 70.0 | 69.8 | 69.7 | 69.6 | 99.4 | 94.0 | 88.0 | 65.5 | 58.0 |
| | <Evaluation item and determination result> | | | | | | | | | | | | |
| | Load | C | B | B | A | A | A | A | D | B | A | A | A |
| | Solubility (transparency of gel) | A | A | A | A | B | B | C | A | A | A | A | C |

(Note)
The molar ratio (c)/(b) in Table 2 was calculated with molecular weights of (b) and (c) set respectively to the following values:
(b) was calculated with ethylene glycol: molecular weight (Mw) = 62 and the molecular weight taken as 1 mol; and
(c) was calculated with terminally hydroxylated polybutadiene: molecular weight (Mw) = 2200 and the molecular weight taken as 1 mol.

[Measurement and Evaluation for Load]

The load of a gel obtained by dissolving 30 parts of the polyurethane gel of each Production Example shown in Table 2 and 70 parts of liquid paraffin by heating at 85° C., followed by cooling to 30° C., was measured using a load measuring machine (available from Rheotech Co., Ltd.) by allowing a needle with a 2-cm-diameter spherical adapter to penetrate 10 mm at 2 cm/min. The evaluation was performed based on the following criteria.
A: 4.50 N or more
B: 2.50 N or more and less than 4.50 N
C: 0.50 N or more and less than 2.50 N
D: Less than 0.50 N

[Measurement and Evaluation for Transparency]

For determining the transparency of the polyurethane gels shown in Table 2, the transmittance at 700 nm was measured using a transmittance measuring instrument (available from SHIMADZU CORPORATION). The evaluation was performed based on the following criteria.
A: 90% or more
B: 85% or more and less than 90%
C: 80% or more and less than 85%
D: Less than 80%

From Table 2, the following facts can be said about the polyurethane gels obtained in Production Examples 2 and 6 to 16.

It is more preferable that the molar ratio (c):(b) (molar ratio (c)/(b)) be 2:3 to 3:2 (0.66 to 1.5).

It is more preferable that the content (mass %) of A (polyurethane) satisfy 1 to 35 mass %, and the content (mass %) of B (cetyl 2-ethylhexanoate (oil agent)) satisfy 65 to 99 mass %.

Oily Body Oils Using Examples 1 to 7 and Comparative Examples 1 to 5

Oily body oils with the compositions shown in Table 3 were prepared by the following production method, and each sample was evaluated for "spreadability", "resilient feeling", "glossy feeling", "no stickiness", and "makeup lasting effect" by the following evaluation methods. Table 3 also shows the results.

TABLE 3

Oily body oil (mass %)

| | | Example | | | | | | | Comparative Example | | | | |
|---|---|---|---|---|---|---|---|---|---|---|---|---|---|
| No. | Component | 1 | 2 | 3 | 4 | 5 | 6 | 7 | 1 | 2 | 3 | 4 | 5 |
| 1 | Polyurethane gel of Production Example 1 (molecular weight: 10000) | 10 | — | — | — | — | — | — | — | — | — | — | — |
| 2 | Polyurethane gel of Production Example 2 (molecular weight: 50000) | — | 10 | — | — | — | 1 | 20 | — | — | — | — | — |
| 3 | Polyurethane gel of Production Example 3 (molecular weight: 100000) | — | — | 10 | — | — | — | — | — | — | — | — | — |
| 4 | Polyurethane gel of Production Example 4 (molecular weight: 50000) | — | — | — | 10 | — | — | — | — | — | — | — | — |
| 5 | Polyurethane gel of Production Example 5 (molecular weight: 100000) | — | — | — | — | 10 | — | — | — | — | — | — | — |

TABLE 3-continued

Oily body oil
(mass %)

| No. | Component | Example 1 | Example 2 | Example 3 | Example 4 | Example 5 | Example 6 | Example 7 | Comparative Example 1 | Comparative Example 2 | Comparative Example 3 | Comparative Example 4 | Comparative Example 5 |
|---|---|---|---|---|---|---|---|---|---|---|---|---|---|
| 6 | Crosslinked silicone gel of Production Comparative Example 1 | — | — | — | — | — | — | — | 10 | — | — | — | — |
| 7 | polysaccharide gel of Production Comparative Example 2 | — | — | — | — | — | — | — | — | 10 | — | 10 | — |
| 8 | Wax oil gel of Production Comparative Example 3 | — | — | — | — | — | — | — | — | — | 10 | — | — |
| 9 | Polyurethane powder | — | — | — | — | — | — | — | — | — | — | 10 | 10 |
| 10 | Liquid paraffin | Balance | Balance | Balance | Balance | Balance | Balance | Balance | Balance | Balance | Balance | Balance | Balance |
| 11 | Glyceryl 2-ethylhexanoate (note 6) | 20 | 20 | 20 | 20 | 20 | 20 | 20 | 20 | 20 | 20 | 20 | 20 |
| 12 | Meadowfoam oil | 5 | 5 | 5 | 5 | 5 | 5 | 5 | 5 | 5 | 5 | 5 | 5 |
| 13 | Rice bran oil | 5 | 5 | 5 | 5 | 5 | 5 | 5 | 5 | 5 | 5 | 5 | 5 |
| 14 | Dialkyl carbonate (note 7) | 5 | 5 | 5 | 5 | 5 | 5 | 5 | 5 | 5 | 5 | 5 | 5 |
| 15 | Decamethylcyclopenta siloxane | 3 | 3 | 3 | 3 | 3 | 3 | 3 | 3 | 3 | 3 | 3 | 3 |
| 16 | Preservative | q.s. | q.s. | q.s. | q.s. | q.s. | q.s. | q.s. | q.s. | q.s. | q.s. | q.s. | q.s. |
| 17 | Flavor | 0.1 | 0.1 | 0.1 | 0.1 | 0.1 | 0.1 | 0.1 | 0.1 | 0.1 | 0.1 | 0.1 | 0.1 |
| <Evaluation Item and determination result> | | | | | | | | | | | | | |
| | Spreadability | A | A | A | A | A | B | B | B | D | D | C | — |
| | Resilient feeling | A | A | A | A | A | B | A | C | D | B | D | — |
| | Glossy feeling | A | A | A | A | A | B | A | D | C | D | D | — |
| | No stickiness | A | A | A | A | A | B | A | B | D | C | C | — |
| | Makeup lasting effect | A | A | A | A | A | B | A | C | C | C | D | — |

(note 6):
T.I.O (available from The Nisshin OilliO Group, Ltd.)
(note 7):
LIALCARB SR-1000/R (available from Mitsui Fine Chemicals, Inc.)

[Production Method]
(1) Components 1 to 16 were uniformly mixed by a disperser.
(2) Component 17 was added to (1), and the mixture was defoamed and filled into a container, to obtain an oily body oil.
[Evaluation]
The oily body oils of Examples 1 to 7 and Comparative Examples 1 to 5 were evaluated for each item of "spreadability", "resilient feeling", "glossy feeling", "no stickiness", and "makeup lasting effect" in 7 grades according to the following evaluation criteria by each of 20 cosmetic evaluation expert panelists and were further determined according to the following criteria using the average of rating by all the panelists.
[Evaluation Criteria]
(Evaluation results):(Rating)
Very good: 6 points
Good: 5 points
Slightly good: 4 points
Usual: 3 points
Slightly bad: 2 points
Bad: 1 point
Very bad: 0 points
[Criteria]
(Average of rating):(Determination)
5.0 or more: A
3.5 or more and less than 5.0: B
1.5 or more and less than 3.5: C
Less than 1.5: D The oily body oils of Examples 1 to 7 were excellent in spreadability, resilient feeling, glossy feeling, no stickiness, and makeup lasting effect. It was confirmed that the oily body oils of Comparative Examples 1 to 5 were each poor in the following points, as compared with the oily body oils of Examples 1 to 7. The oily body oil of Comparative Example 1 had low elasticity and low transparency of the crosslinked silicone gel and thus was poor particularly in resilient feeling and glossy feeling. Further, the oily body oil of Comparative Example 2 had comparatively high transparency of the polysaccharide gel of the dextrin fatty acid ester but had sticky feeling specific to sugars and further had low elasticity, thereby having bad spreadability and being poor in resilient feeling and no stickiness. Further, the oily body oil of Comparative Example 3 was poor in clarity and elastic feeling of the wax oil gel and was hard, therefore having bad spreadability and poor glossy feeling. The oily body oil of Comparative Example 4 using the polyurethane powder and the polysaccharide gel instead of the polyurethane gel of the present invention was insufficient in spreadability and no stickiness and was also poor in resilient feeling, glossy feeling, and makeup lasting effect. Comparative Example 5 using the polyurethane powder instead of the polyurethane gel of the present invention underwent precipitation of the polyurethane powder, and the evaluation thereof was difficult.

Example 8: Emulsion Skin Lotion (Component): (mass %)
1. Cetyl alcohol: 0.2

2. Polyurethane gel of Production Example 1: 0.2
3. Phospholipid-phytosterol mixture (15:85) (Note 8): 0.5
4. Polyoxyethylene (40 mol)-hardened castor oil: 0.1
5. Tocopherol acetate: 0.5
6. Triethanolamine stearate: 0.5
7. Purified water: balance
8. Ethanol: 10.0
9. Flavor: 0.1
(Note 8) Available from NIPPON FINE CHEMICAL CO., LTD.
(Fabrication Method)
(1) Components 1 to 6 were heated to 75° C. and were uniformly mixed and dissolved.
(2) Components 7 and 8 were heated to 75° C. and were uniformly mixed and dissolved.
(3) (2) was added to (1), followed by emulsification.
(4) (3) was cooled, and component 9 was added thereto, to obtain an emulsion skin lotion.

The emulsion skin lotion of Example 8 was excellent in "spreadability", "resilient feeling", "glossy feeling", "no stickiness", and "makeup lasting effect".

Example 9: Milky Lotion (Component): (mass %)
1. Stearic acid: 0.5
2. Polyoxyethylene sorbitan monostearate (20EO): 1.0
3. Polyoxypropylene sorbitol tetraoleate (40EO): 1.0
4. Behenyl alcohol: 1.5
5. Liquid paraffin: 2.0
6. Glyceryl tri-2-ethylhexanoate: 5.0
7. Polyurethane gel of Production Example 2: 2.0
8. Acrylic acid-methacrylic acid alkyl ester copolymer: 0.1
9. Xanthan gum: 0.1
10. Sodium hydroxide: 0.05
11. 1,3-Butylene glycol: 8.0
12. Preservative: q.s.
13. Flavor: 0.1
14. Purified water: balance
(Fabrication Method)
(1) Components 1 to 7 were uniformly mixed at 80° C.
(2) Components 8 to 14 were uniformly mixed at 80° C.
(3) (2) was added to (1), followed by emulsification.
(4) (3) was cooled under stirring, to obtain a milky lotion.

The milky lotion of Example 9 was excellent in "spreadability", "resilient feeling", "glossy feeling", "no stickiness", and "makeup lasting effect".

Example 10: O/W Cream (Component): (mass %)
1. Decaglyceryl pentaoleate: 2.5
2. Behenyl alcohol: 1.5
3. Vaseline: 3.0
4. Heavy liquid isoparaffin: 1.0
5. Glyceryl tri-2-ethylhexanoate: 1.0
6. Polyurethane gel of Production Example 3: 4.0
7. Purified water: balance
8. Glycerin: 7.0
9. Acrylic acid-methacrylic acid alkyl ester copolymer: 0.2
10. Sodium hydroxide: 0.09
11. Preservative: q.s.
12. Flavor: 0.1
(Fabrication Method)
(1) Components 1 to 6 were uniformly mixed at 80° C.
(2) Components 7 to 12 were uniformly mixed at 80° C.
(3) (2) was added to (1), followed by emulsification.
(4) (3) was cooled under stirring, to obtain a cream.

The O/W cream of Example 10 was excellent in "spreadability", "resilient feeling", "glossy feeling", "no stickiness", and "makeup lasting effect".

Example 11: W/O Cream (Component): (mass %)
1. Microcrystalline wax: 1.5
2. Beeswax: 1.5
3. Cetyl alcohol: 3.0
4. Polyurethane gel of Production Example 4: 3.0
5. Hydrogenated soybean phospholipid: 1.0
6. Squalane: 35.0
7. Sorbitan sesquioleic acid ester: 3.0
8. Propylene glycol: 10.0
9. Preservative: q.s.
10. Flavor: 0.1
11. Purified water: balance
(Fabrication Method)
(1) Components 1 to 7 were heated to 75° C. and were uniformly mixed and dissolved.
(2) Components 8 and 11 were heated to 75° C. and were uniformly mixed and dissolved.
(3) (2) was added to (1), followed by emulsification.
(4) (3) was cooled, and components 9 and 10 were added thereto, to obtain a W/O cream.

The W/O cream of Example 11 was excellent in "spreadability", "resilient feeling", "glossy feeling", "no stickiness", and "makeup lasting effect".

Example 12: Oil Cleansing (Component): (mass %)
1. Polyoxyethylene sorbit tetraoleate: 8.0
2. Polyglyceryl diisostearate: 0.5
3. Liquid paraffin: balance
4. Glyceryl tri-2-ethylhexanoate: 25.0
5. Polyurethane gel of Production Example 5: 1.0
6. Preservative: q.s.
7. Flavor: 0.1
(Fabrication Method)
(1) Components 1 to 7 were uniformly mixed at normal temperature, to obtain an oil cleansing.

The oil cleansing of Example 12 was excellent in "spreadability", "resilient feeling", "glossy feeling", "no stickiness", and "makeup lasting effect".

Example 13: Cleansing Cream (Component): (mass %)
1. Stearic acid: 3.0
2. Cetanol: 2.0
3. Polyoxypropylene sorbitol tetraoleate (40EO): 1.0
4. Polyoxyethylene sorbitan monostearate (20EO): 1.0
5. Glyceryl tri-2-ethylhexanoate: 20.0
6. Liquid paraffin: 20.0
7. Polyurethane gel of Production Example 1: 2.0
8. Acrylic acid-methacrylic acid alkyl ester copolymer: 0.1
9. 1,3-Butylene glycol: 7.0
10. Sodium hydroxide: 0.05
11. Purified water: balance
12. Preservative: q.s.
13. Flavor: 0.1
(Fabrication method)
(1) Components 1 to 7 were uniformly mixed at 80° C.
(2) Components 8 to 13 were uniformly mixed at 80° C.

(3) (1) was added to (2), followed by emulsification.
(4) (3) was cooled under stirring, to obtain a cleansing cream.

The cleansing cream of Example 13 was excellent in "spreadability", "resilient feeling", "glossy feeling", "no stickiness", and "makeup lasting effect".

Example 14: Styling Water (Component): (mass %)
1. Ethanol: 15.0
2. Stearyltrimethylammonium chloride: 0.2
3. Polyoxyethylene isostearate-hardened castor oil: 0.2
4. Polyurethane gel of Production Example 2: 0.1
5. Purified water: balance
6. Hydroxypropyl cellulose: 0.01
7. Highly polymerized methylpolysiloxane emulsion (Note 9): 2.0
8. Preservative: q.s.
9. Flavor: 0.1
(Note 9) BY11-007 (available from Dow Corning Toray Co., Ltd.)
(Fabrication Method)
(1) Components 1 to 9 were uniformly mixed at normal temperature, to obtain a styling water.

The styling water of Example 14 was excellent in "spreadability", "resilient feeling", "glossy feeling", "no stickiness", and "makeup lasting effect".

Example 15: Hair Wax (Component): (mass %)
1. Purified water: balance
2. Propylene glycol: 10.0
3. Polyethylene glycol monostearate: 3.0
4. Vaseline: 10.0
5. Paraffin wax: 3.0
6. Cetostearyl alcohol: 3.0
7. Behenyl alcohol: 3.0
8. Polyurethane gel of Production Example 3: 2.0
9. Ethanol: 5.0
10. Purified water 15.0
11. Vinylpyrrolidone: 1.0
12. Acrylic acid-methacrylic acid alkyl ester copolymer: 0.15
13. Sodium hydroxide: 0.05
14. Preservative: q.s.
15. Flavor: 0.1
(Fabrication Method)
(1) Components 1 to 3 were uniformly mixed at 80° C.
(2) Components 4 to 8 were uniformly mixed at 80° C.
(3) (2) was added to (1), followed by emulsification.
(4) Components 9 to 15 were added to (3), and the mixture was cooled under stirring, to obtain a hair wax.

The hair wax of Example 15 was excellent in "spreadability", "resilient feeling", "glossy feeling", "no stickiness", and "makeup lasting effect".

Example 16: O/W Mascara (Component): (mass %)
1. Stearic acid: 2.0
2. Beeswax: 10.0
3. Cetostearyl alcohol: 1.0
4. Polyoxyethylene sorbitan monooleate (20EO): 1.5
5. Sorbitan sesquioleate: 0.5
6. Polyurethane gel of Production Example 4: 3.0
7. Black iron oxide: 5.0
8. Anhydrous silicic acid: 3.0
9. Purified water: balance
10. 1,3-Butylene glycol: 10.0
11. Triethanolamine: 1.5
12. Alkyl acrylate copolymer emulsion (Note 10): 30.0
13. Preservative: q.s.
14. Flavor: 0.1
(Note 10) Yodosol 32A707 (with a solid content of 45 mass %) (available from Nippon NSC Co.)
(Fabrication Method)
(1) Components 1 to 3 were uniformly mixed at 80° C.
(2) Components 4 to 8 were treated using a roller.
(3) Components 9 to 14 were uniformly mixed at 80° C.
(4) After mixing (1) and (2), (3) was added thereto, followed by emulsification.
(5) (4) was cooled, to obtain an O/W mascara.

The O/W mascara of Example 16 was excellent in "spreadability", "resilient feeling", "glossy feeling", "no stickiness", and "makeup lasting effect".

Example 17: Paste Lip Gloss (Component): (mass %)
1. Polyurethane gel of Production Example 5: 2.0
2. Diisostearyl malate: 10.0
3. Stearyl lactate: 10.0
4. Hydrogenated polyisobutene: 30.0
5. Triethylhexanoin: balance
6. Liquid paraffin: 5.0
7. Microcrystalline wax: 2.0
8. 12-Hydroxystearic acid: 0.1
9. α Olefin-vinylpyrrolidone copolymer (Note 11): 0.5
10. Anhydrous silicic acid (Note 12): 3.5
11. Colcothar: 0.1
12. Red No. 201: 0.3
13. Black iron oxide: 0.05
14. Titanium oxide: 0.2
15. Soybean phospholipid: 0.01
16. 2-Ethylhexyl p-methoxycinnamate: 3.0
17. Preservative: q.s.
18. Flavor: 0.1
(Note 11) ANTARON V-220 (available from ISP)
(Note 12) AEROSIL 200 (available from Japan Aerosil Inc.)
(Fabrication Method)
(1) Components 1 to 9 were mixed and dissolved at 100° C.
(2) Components 10 to 18 were added to (1), and were uniformly mixed and dispersed therein.
(3) (2) was poured into a tube, followed by cooling, to obtain a paste lip gloss.

The paste lip gloss of Example 17 was excellent in "spreadability", "resilient feeling", "glossy feeling", "no stickiness", and "makeup lasting effect".

Example 18: Stick Lipstick (Component): (mass %)
1. Polyethylene wax: 10.0
2. Carnauba wax: 5.0
3. Paraffin wax: 2.0
4. Cetyl 2-ethylhexanoate: balance
5. Polyurethane gel of Production Example 1: 2.0
6. Liquid paraffin: 10.0
7. Isotridecyl isononanoate: 10.0
8. Red No. 202: 0.5
9. Yellow No. 4: 2.0
10. Titanium oxide: 0.5

11. Black iron oxide: 0.1
12. α-Tocopherol: 0.5
13. Flavor: 0.1
(Fabrication Method)
(1) Components 1 to 7 were uniformly mixed and dissolved at 100° C.
(2) Components 8 to 13 were added to (1) and were uniformly mixed therein.
(3) (2) was poured into a container, followed by cooling, to obtain a stick lipstick.

The stick lipstick of Example 18 was excellent in "spreadability", "resilient feeling", "glossy feeling", "no stickiness", and "makeup lasting effect".

Example 19: Oily Eye Shadow (Component): (mass %)
1. Dextrin fatty acid ester (Note 13): 2.0
2. Polyurethane gel of Production Example 2: 1.0
3. Diisostearyl malate: 2.5
4. 2-Cetyl ethylhexanoate: 13.0
5. Dextrin laurate: 2.0
6. Dextrin myristate: 5.0
7. Dextrin behenate: 5.0
8. Liquid paraffin: balance
9. Hydrogenated polyisobutene: 1.5
10. Anhydrous silicic acid: 6.0
11. Nylon powder: 5.0
12. Silicone-treated talc (Note 14): 5.5
13. Red No. 202: 0.05
14. Yellow No. 4, aluminum lake: 0.05
15. Blue No. 1, aluminum lake: 0.05
16. Titanium mica: 1.5
17. Preservative: q.s.
18. Flavor: 0.1
(Note 13) Rheopearl TT (available from Chiba Flour Milling Co., Ltd.)
(Note 14) Treated with 5 mass % of dimethylpolysiloxane
(Fabrication Method)
(1) Components 1 to 9 were mixed and dissolved at 100° C.
(2) Components 10 to 18 were added to (1), and were uniformly mixed and dispersed therein.
(3) (2) was poured into a container, followed by cooling and solidification, to obtain an oily eye color.

The oily eye shadow of Example 19 was excellent in "spreadability", "resilient feeling", "glossy feeling", "no stickiness", and "makeup lasting effect".

Example 20: Solid Powder Foundation (Component): (mass %)
1. Dimethylpolysiloxane-treated talc: 30.0
2. Dimethylpolysiloxane-treated mica: 15.0
3. Dimethylpolysiloxane-treated titanium oxide: 15.0
4. Dimethylpolysiloxane-treated sericite: balance
5. Synthetic phlogopite: 5.0
6. Yellow iron oxide: 2.0
7. Colcothar: 0.5
8. Black iron oxide: 0.2
9. Preservative: q.s.
10. Polyurethane gel of Production Example 3: 1.0
11. Liquid paraffin: 3.0
12. Dimethylpolysiloxane: 1.0
13. Glyceryl 2-ethylhexanoate: 2.0
14. Flavor: 0.1
(Fabrication Method)
(1) Components 1 to 9 were uniformly dispersed at 75° C. using a Henschel mixer (available from MITSUI MIIKE MACHINERY CO., LTD).
(2) Components 10 to 13 were uniformly mixed and dissolved.
(3) (2) and 14 were added to (1) under stirring with the Henschel mixer and were uniformly dispersed therein.
(4) (3) was pulverized with a pulverizer.
(5) (4) was filled into a gold plate, followed by compression forming, to obtain a solid powder foundation.

The solid powder foundation of Example 20 was excellent in "spreadability", "resilient feeling", "glossy feeling", "no stickiness", and "makeup lasting effect".

Example 21: Solid Powder Eye Shadow (Component): (mass %)
1. Dimethylpolysiloxane-treated synthetic gold mica: 10.0
2. Dimethylpolysiloxane-treated talc: balance
3. Titanium oxide-coated mica: 30.0
4. Boron nitride: 5.0
5. Polyethylene terephthalate-aluminum-epoxy laminate powder: 5.0
6. Ultramarine: 2.0
7. Red No. 202: 0.5
8. Alkyl polyacrylate: 1.0
9. Preservative: q.s.
10. Polyurethane gel of Production Example 4: 1.0
11. Liquid paraffin: 3.0
12. Dimethylpolysiloxane: 2.0
13. Glyceryl 2-ethylhexanoate: 2.0
14. Flavor: 0.1
(Fabrication Method)
(1) Components 1 to 9 were uniformly dispersed at 75° C. using a Henschel mixer (available from MITSUI MIIKE MACHINERY CO., LTD).
(2) Components 10 to 13 were uniformly mixed and dissolved.
(3) (2) and 14 were added to (1) under stirring with the Henschel mixer and were uniformly dispersed therein.
(4) (3) was pulverized with a pulverizer.
(5) (4) was filled into a gold plate, followed by compression forming, to obtain a solid powder eye shadow.

The solid powder eye shadow of Example 21 was excellent in "spreadability", "resilient feeling", "glossy feeling", "no stickiness", and "makeup lasting effect".

Example 22: Solid Powder Face Color (Component): (mass %)
1. Mica: 20.0
2. Talc: balance
3. Titanium oxide-coated mica: 10.0
4. Ultramarine: 0.5
5. Red No. 226: 0.2
6. Alkyl polyacrylate: 1.0
7. Preservative: q.s.
8. Polyurethane gel of Production Example 5: 1.0
9. Liquid paraffin: 2.0
10. Dimethylpolysiloxane 1.0
11. Glyceryl 2-ethylhexanoate: 1.0
12. Flavor: 0.1
(Fabrication Method)
(1) Components 1 to 7 were uniformly dispersed at 75° C. using a Henschel mixer (available from MITSUI MIIKE MACHINERY CO., LTD).

(2) Components 8 to 11 were heated to 65° C. to be uniformly mixed and dissolved.
(3) (2) and 12 were added to (1) under stirring with the Henschel mixer and were uniformly dispersed therein.
(4) (3) was pulverized with a pulverizer.
(5) (4) was filled into a gold plate, followed by compression forming, to obtain a solid powder face color.

The solid powder face color of Example 22 was excellent in "spreadability", "resilient feeling", "glossy feeling", "no stickiness", and "makeup lasting effect".

Example 23: Stick Concealer (Component): (mass %)
1. Paraffin wax: 5.0
2. Polyethylene wax: 5.0
3. Candelilla wax: 2.0
4. Polyurethane gel of Production Example 1: 2.0
5. Glyceryl tri-2-ethylhexanoate: 15.0
6. Methylphenyl polysiloxane: 5.0
7. Acetic acid liquid lanolin 10.0
8. 2-Ethylhexyl p-methoxycinnamate: 5.0
9. Titanium oxide: 20.0
10. Yellow iron oxide: 2.0
11. Colcothar: 0.5
12. Black iron oxide: 0.2
13. Mica: 7.0
14. Preservative: q.s.
(Fabrication Method)
(1) Components 1 to 8 were mixed and dissolved at 100° C.
(2) Components 9 to 14 were uniformly mixed with (1) at 90° C.
(3) (2) was treated using three rollers.
(4) (3) was defoamed, dissolved at 85° C., and filled into a capsule, followed by cooling to 4° C., to obtain a stick concealer.

The stick concealer of Example 23 was excellent in "spreadability", "resilient feeling", "glossy feeling", "no stickiness", and "makeup lasting effect".

Example 24: W/O Sunscreen (Component): (mass %)
1. Zinc oxide: 2.0
2. Silicone-coated fine particle titanium oxide: 5.0
3. Glyceryl tri(capryl caprate): 5.0
4. Glyceryl tri-2-ethylhexanoate: 3.0
5. Octyl palmitate: 3.0
6. 2-Ethylhexyl p-methoxycinnamate: 10.0
7. Decamethylcyclopentasiloxane: 10.0
8. Methylpolysiloxane-cetylmethylpolysiloxane-poly(oxyethylene-oxypropylene)methylpolysiloxane copolymer (Note 15): 1.8
9. Polyurethane gel of Production Example 2: 1.0
10. Preservative: q.s.
11. Sodium chloride: 0.3
12. Purified water: balance
13. Dipropylene glycol 5.0
14. Ethanol: 5.0
15. Flavor: 0.1
(Note 15) ABIL EM-90 (available from EVONIC GOLDSCHMIDT GMBH)
(Fabrication Method)
(1) Components 3 and 4 were dissolved by heating, and components 1 and 2 were then added thereto and were uniformly dispersed therein using a roller.
(2) Components 5 to 10 were dissolved at 70° C. (1) was then added thereto at 60° C., and was uniformly mixed and dissolved therein.
(3) Components 11 to 13 were mixed and dissolved, and were then added to (2) at 60° C., followed by emulsification.
(4) Components 14 and 15 were added to (3) and were uniformly mixed therein, to obtain a W/O sunscreen.

The W/O sunscreen of Example 24 was excellent in "spreadability", "resilient feeling", "glossy feeling", "no stickiness", and "makeup lasting effect".

Example 25: W/O Foundation (Component): (mass %)
1. Polyoxyethylenemethylsiloxane-polyoxypropyleneoleylmethylsiloxane-dimethylsiloxane copolymer (Note 16): 2.0
2. PEG-3 dimethicone (Note 17): 1.0
3. Cyclopentasiloxane: 20.0
4. Silicone-treated red iron oxide: 1.0
5. Silicone-treated yellow iron oxide: 1.5
6. Silicone-treated black iron oxide: 0.5
7. Silicone-treated titanium oxide: 10.0
8. Silicone-treated talc: 5.0
9. Glyceryl tri-2-ethylhexanoate: 5.0
10. Polyurethane gel of Production Example 3: 1.0
11. Sorbitan sesquioleate: 0.5
12. Purified water: balance
13. 1,3-Butylene glycol: 15.0
14. Sodium chloride: 0.5
15. Preservative: q.s.
16. Flavor: 0.1
(Note 16) KF-6026 (available from Shin-Etsu Chemical Co., Ltd.)
(Note 17) KF-6015 (available from Shin-Etsu Chemical Co., Ltd.)
(Fabrication Method)
(1) Components 1 to 3 were uniformly mixed.
(2) Components 4 to 11 were uniformly dispersed using a roller.
(3) (2) was added to (1) and was uniformly mixed.
(4) Components 12 to 16 were added to (3), followed by emulsification, to obtain a W/O foundation.

The W/O foundation of Example 25 was excellent in "spreadability", "resilient feeling", "glossy feeling", "no stickiness", and "makeup lasting effect".

Example 26: O/W Foundation (Component): (mass %)
1. Polyoxyethylene sorbitan monooleate (20EO): 0.5
2. Sorbitan sesquioleate: 0.5
3. 1,3-Butylene glycol: 10.0
4. Silicone-treated titanium oxide: 10.0
5. Silicone-treated colcothar: 0.4
6. Silicone-treated yellow iron oxide: 2.0
7. Silicone-treated black iron oxide: 0.1
8. Silicone-treated talc: 5.0
9. Carboxyvinyl polymer 0.3
10. Triethanolamine: 1.0
11. Purified water: balance
12. Ethanol: 2.0
13. Stearic acid: 1.0
14. Behenyl alcohol: 0.5
15. Liquid paraffin: 5.0
16. Polyurethane gel of Production Example 4: 1.0
17. Glyceryl tri-2-ethylhexanoate: 1.0
18. 2-Ethylhexyl paramethoxycinnamate: 2.0

19. Vaseline: 0.5
20. Preservative: q.s.
21. Flavor: 0.1
(Fabrication Method)
(1) Components 1 to 8 were uniformly dispersed using a roller.
(2) Components 9 to 12 were uniformly mixed.
(3) (1) was added to (2) and was uniformly mixed therein.
(4) Components 13 to 20 were mixed and dissolved at 80° C.
(5) (4) was added to (3) at 80° C., followed by emulsification.
(6) (5) was cooled, and component 21 was added thereto, to obtain an O/W foundation.

The O/W foundation of Example 26 was excellent in "spreadability", "resilient feeling", "glossy feeling", "no stickiness", and "makeup lasting effect".

Example 27: Oily Solid Foundation (Component): (mass %)
1. Talc: 15.0
2. Mica: 10.0
3. Silicone-treated titanium oxide: 15.0
4. Silicone-treated colcothar: 1.0
5. Silicone-treated yellow iron oxide: 3.0
6. Silicone-treated black iron oxide: 0.2
7. Polyethylene wax: 7.0
8. Microcrystalline wax: 6.0
9. Glyceryl tri-2-ethylhexanoate: balance
10. Polyurethane gel of Production Example 5: 3.0
11. Dimethylpolysiloxane: 5.0
12. Liquid paraffin: 20.0
13. Polyoxyethylenemethylsiloxane-polyoxypropyleneoleylmethylsiloxane-dimethylsiloxane copolymer (Note 16): 2.0
14. Preservative: q.s.
15. Flavor: 0.1
(Note 16) KF-6026 (available from Shin-Etsu Chemical Co., Ltd.)
(Fabrication Method)
(1) Components 7 to 14 were dissolved by heating at 90° C.
(2) Components 1 to 6 were added to (1) and were uniformly dispersed using a roller.
(3) Component 15 was added to (2), dissolved at 80° C., and filled into a gold plate, to obtain an oily solid foundation.

The oily solid foundation of Example 27 was excellent in "spreadability", "resilient feeling", "glossy feeling", "no stickiness", and "makeup lasting effect".

Example 28: Makeup Base (Component): (mass %)
1. Cetostearyl alcohol: 2.0
2. 2-Ethylhexyl p-methoxycinnamate: 5.0
3. Polyurethane gel of Production Example 1: 2.0
4. Glyceryl tri-2-ethylhexanoate: 3.0
5. Purified water: balance
6. Sodium N-stearoyl-N-methyl taurate: 0.5
7. Carboxyvinyl polymer: 0.1
8. Acrylic acid-methacrylic acid alkyl ester copolymer: 0.1
9. Sodium hydroxide: 0.05
10. Ethanol: 10.0
11. 1,3-Butylene glycol: 10.0
12. Preservative: q.s.
13. Flavor: 0.1
(Fabrication Method)
(1) Components 1 to 4 were uniformly dissolved at 80° C.
(2) Components 5 to 13 were uniformly dissolved at 80° C.
(3) (1) was added to (2), followed by emulsification.
(4) Component 14 was added to (3), followed by cooling, to obtain a makeup base.

The makeup base of Example 28 was excellent in "spreadability", "resilient feeling", "glossy feeling", "no stickiness", and "makeup lasting effect".

Example 29: Body Milk (Component): (mass %)
1. Stearic acid: 1.0
2. Polyoxyethylene sorbitan monooleate (20EO): 0.5
3. Sorbitan sesquioleate: 0.5
4. Behenyl alcohol: 0.5
5. Glyceryl 2-ethylhexanoate: 2.0
6. Liquid paraffin: 2.0
7. Polyurethane gel of Production Example 2: 2.0
8. Ethanol: 10.0
9. Dipropylene glycol: 10.0
10. Triethanolamine: 1.0
11. Purified water: balance
12. Glycerin: 5.0
13. 1,3-Butylene glycol: 5.0
14. Acrylic acid-methacrylic acid alkyl ester copolymer: 0.2
15. Preservative: q.s.
16. Flavor: 0.1
(Fabrication Method)
(1) Components 1 to 7 were uniformly dissolved at 80° C.
(2) Components 8 to 16 were uniformly dissolved at 80° C.
(3) (1) was added to (2), followed by emulsification.
(4) (3) was stirred and cooled, to obtain a body milk.

The body milk of Example 29 was excellent in "spreadability", "resilient feeling", "glossy feeling", "no stickiness", and "makeup lasting effect".

Example 30: Remover (Component): (mass %)
1. 1,3-Butylene glycol: 15.0
2. Alkyl acrylate copolymer emulsion (Note 18): 2.5
3. L-Arginine: 0.5
4. Purified water: balance
5. Light liquid isoparaffin: 3.0
6. Polyurethane gel of Production Example 3: 0.5
7. Preservative: q.s.
8. Flavor: 0.1
(Note 18) Yodosol 32A707 (with a solid content of 45 mass %) (available from Nippon NSC Co.)
(Fabrication Method)
(1) Components 1 to 4 were uniformly mixed.
(2) Components 5 to 8 were added to (1) at 60° C., followed by emulsification.
(3) (2) was cooled under stirring, to obtain a remover.

The remover of Example 30 was excellent in "spreadability", "resilient feeling", "glossy feeling", "no stickiness", and "makeup lasting effect".

Example 31: Non-Aqueous Mascara (Component): (mass %)
1. Pentaerythrityl rosinate: 10.0
2. Candelilla resin: 3.0
3. Beeswax: 2.0
4. Ceresin wax: 2.0

5. Dextrin palmitate: 2.0
6. Trimethylsiloxysilicate: 3.0
7. Dimethyldistearylammonium hectorite: 5.0
8. Propione carbonate: 1.0
9. Light liquid isoparaffin: balance
10. Polyurethane gel of Production Example 4: 2.0
11. Black iron oxide: 5.0
12. Silica: 3.0
13. Talc: 5.0

(Fabrication Method)
(1) Components 1 to 5 were heated to 110° C.
(2) Components 6 to 10 were added to (1) and were mixed therein.
(3) Components 11 to 13 were added to (2) and were mixed therein.
(4) (3) was treated using a roller, to obtain a non-aqueous mascara.

The non-aqueous mascara of Example 31 was excellent in "spreadability", "resilient feeling", "glossy feeling", "no stickiness", and "makeup lasting effect".

Example 32: Oily Eyeliner (Component): (mass %)
1. Ceresin wax: 11.0
2. Polyisobutylene: 16.0
3. Polyethylene wax: 8.0
4. Light liquid isoparaffin: balance
5. Polyurethane gel of Production Example 5: 2.0
6. Silicone-treated black iron oxide: 15.0
7. Silicone-treated talc: 5.0
8. Preservative: q.s.
9. Flavor: 0.1

(Fabrication Method)
(1) Components 1 to 5 were heated to 100° C. and were uniformly mixed.
(2) Components 6 to 9 were heated to 80° C. and were uniformly mixed.
(3) (2) was added to (1) and was uniformly mixed therein.
(4) (3) was treated using a roller, to obtain an oily eyeliner.

The oily eyeliner of Example 32 was excellent in "spreadability", "resilient feeling", "glossy feeling", "no stickiness", and "makeup lasting effect".

INDUSTRIAL APPLICABILITY

The polyurethane gel composition of the present invention can provide an oil-soluble gel film that is exceptionally excellent in any point of transparency, high gloss, elasticity, and resilience, and thus is an exceptionally useful invention, particularly, in the technical field of cosmetics.

The invention claimed is:

1. A cosmetic comprising a polyurethane gel composition comprising A and B, wherein A gels B,
   wherein the polyurethane gel composition has a transmittance at a wavelength of 700 nm of 90% or more,
   wherein A is contained in an amount of 1 to 35 mass % in the polyurethane gel composition,
   wherein
   A represents an oil-soluble polyurethane obtained by reaction of
   (a) a hydrogenated polybutadiene having isocyanate groups at the terminals and being an isocyanate compound represented by formula (2):

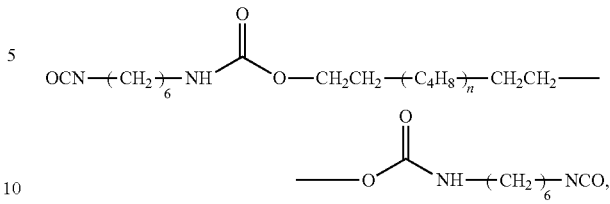

wherein n represents an integer of 10 to 100, and
   (b) a glycol represented by HO—$R_3$—OH, wherein $R_3$ represents a linear or branched C2 to C6 alkylene group,
   or
   A represents an oil-soluble polyurethane obtained by reaction of
   (c) a hydrogenated polybutadiene having hydroxyl groups at the terminals, the hydrogenated polybutadiene being represented by formula (3):

wherein n represents an integer of 10 to 100, and
   (d) a diisocyanate compound represented by formula (4):

and
   the (b) glycol represented by HO—$R_3$—OH, wherein $R_3$ represents a linear or branched C2 to C6 alkylene group, and
   B represents an oil agent.

2. The cosmetic according to claim 1, wherein (a) in A is obtained by reaction of (c) and (d).

3. The cosmetic according to claim 1, wherein the polyurethane represented by A has an average molecular weight (Mw) of 10000 to 100000.

4. The cosmetic according to claim 1, wherein the oil agent represented by B is an oil agent in liquid form at 25° C.

5. The cosmetic according to claim 1, wherein the oil agent represented by B is one or more selected from a hydrocarbon oil, an ester oil having 0 or 1 hydroxyl group, and a silicone oil.

6. The cosmetic according to claim 1, wherein the polyurethane gel composition is a polyurethane gel composition, wherein a gel for measuring load obtained by dissolving 30 parts of the polyurethane gel composition and 70 parts of liquid paraffin by heating at 85° C., followed by cooling, shows a load of 0.20 to 10.00 N when a needle with a 2-cm-diameter spherical adapter is allowed to penetrate 10 mm at 2 cm/min.

7. The cosmetic according to claim 1, wherein the polyurethane gel composition has a gel resilience.

8. The cosmetic according to claim 1, wherein the cosmetic is selected from a group consisting of an eye shadow, a foundation, a makeup base, a sunscreen, a lipstick, and a mascara.

9. The cosmetic according to claim 1, wherein A represents an oil-soluble polyurethane obtained by reaction of (a) and (b) in molar ratio (a):(b)=2:3 to 3:2; or wherein A represents an oil-soluble polyurethane obtained by reaction of (c), (d) and (b) in molar ratio (c):(b)=2:3 to 3:2.

10. The cosmetic according to claim 9, wherein (a) or (c) has an average molecular weight (Mw) of 1000 to 3000.

11. The cosmetic according to claim 9, wherein a mass ratio of A to B (A:B) in the polyurethane gel composition is 1:99 to 35:65.

12. The cosmetic according to claim 1, wherein the cosmetic comprises a surface-treated powder, wherein a surface of the powder is coated with the polyurethane gel composition as a surface treating agent.

13. The cosmetic according to claim 9, wherein a mass ratio of A to B (A:B) in the polyurethane gel composition is 6:94 to 34.5:65.5.

14. The cosmetic according to claim 1, wherein A represents an oil-soluble polyurethane obtained by reaction of (a) and (b) in molar ratio (a):(b)=9:10 to 10:9; or wherein A represents an oil-soluble polyurethane obtained by reaction of (c), (d), and (b) in molar ratio (c):(b)=9:10 to 10:9; and wherein a mass ratio of A to B (A:B) in the polyurethane gel composition is 12:88 to 34.5:65.5.

15. The cosmetic according to claim 1, wherein the cosmetic comprises the polyurethane gel composition in an amount of 0.1 to 20 mass %.

* * * * *